(12) United States Patent
He et al.

(10) Patent No.: US 9,029,542 B2
(45) Date of Patent: May 12, 2015

(54) SUBSTITUTED PHENOXYETHYL (ISOPROPYL) ACYLOXYALKYL PHOSPHONATE COMPRISING PHOSPHORUSHETEROCYCLIC RING AND HAVING HERBICIDAL ACTIVITY, AND PREPARATION THEREFOR

(71) Applicant: Central China Normal University, Wuhan, Hubei (CN)

(72) Inventors: Hongwu He, Hubei (CN); Wei Wang, Hubei (CN); Na Zuo, Hubei (CN); Xijun Sheng, Hubei (CN); Hao Peng, Hubei (CN); Xiaosong Tan, Hubei (CN)

(73) Assignee: Central China Normal University, Wuhan, Hubei (CN)

( * ) Notice: Subject to any disclaimer, the term of this patent is extended or adjusted under 35 U.S.C. 154(b) by 59 days.

(21) Appl. No.: 14/185,721

(22) Filed: Feb. 20, 2014

(65) Prior Publication Data
US 2014/0171644 A1 Jun. 19, 2014

Related U.S. Application Data

(63) Continuation of application No. PCT/CN2012/081013, filed on Sep. 5, 2012.

(30) Foreign Application Priority Data

Sep. 6, 2011 (CN) .......................... 2011 1 0261080
Aug. 27, 2012 (CN) .......................... 2012 1 0307798

(51) Int. Cl.
*A01N 57/36* (2006.01)
*C07F 9/6571* (2006.01)
*C07F 9/6574* (2006.01)

(52) U.S. Cl.
CPC .......... *A01N 57/36* (2013.01); *C07F 9/657118* (2013.01); *C07F 9/65742* (2013.01); *C07F 9/65748* (2013.01)

(58) Field of Classification Search
None
See application file for complete search history.

(56) References Cited

U.S. PATENT DOCUMENTS 3,287,448 A 11/1966 Ratz

FOREIGN PATENT DOCUMENTS

| CN | 1060480 C | 1/2001 |
| CN | 100412078 C | 8/2008 |

OTHER PUBLICATIONS

Zuo et al., 63(2) Acta Crystallographica Section E: Structure Reports Online o794-o795 (2007) (CAS Abstract).*
Shag, Rui-Lian et al., Studies on Synthesis and Biological Activity of Caged Bicyclophosphate Compounds, Chemical Journal of Chinese Universities, 1991, p. 1063-1065, vol. 12, No. 8.
Wu, You-Bin et al., Synthesis and Bioactivity of 4-Alkyl-3-cyano-caged Bicyclic-phosphates, Chinese Journal of Organic Chemistry, 2008, p. 1273-1277, vol. 28, No. 7.
State Intellectual Property Office of the People's Republic of China, "International Search Report", Dec. 13, 2012, China.

* cited by examiner

*Primary Examiner* — Timothy R Rozof
(74) *Attorney, Agent, or Firm* — Tim Tingkang Xia, Esq.; Morris, Manning & Martin, LLP

(57) ABSTRACT

A substituted phenoxyethyl(isopropyl)acyloxyalkyl phosphonate having phosphorusheterocyclic ring and having herbicidal activity, with a general formula of I, wherein R represents 5,5-dimethyl-1,3,2-dioxaphosphorinan-2-one-2-yl, or 1-oxo-1-phospha-2,6,7-trioxabicyclo[2,2,2]octan-4-yl, or 1-sulfo-1-phospha-2,6,7-trioxabicyclo 2,6,7-trioxabicyclo [2,2,2]octan-4-yl; $R^1$ represents H, C1-C4 alkyl, phenyl, furyl, pyridyl, or phenyl substituted with methyl, methoxyl, nitro or chloro; $R^2$ represents H, methyl, and methyl only if R in the general formula I is 1-sulfo-1-phospha-2,6,7-trioxabicyclo[2,2,2]octan-4-yl as phosphorusheterocyclic ring; X and Y represent H, halogen, C1-C4 alkyl or trifluoromethyl, and X and Y are the same or different. The compounds according to the present invention may be used as active component of dicotyledonous broadleaf weed herbicides.

3 Claims, No Drawings

SUBSTITUTED PHENOXYETHYL (ISOPROPYL) ACYLOXYALKYL PHOSPHONATE COMPRISING PHOSPHORUSHETEROCYCLIC RING AND HAVING HERBICIDAL ACTIVITY, AND PREPARATION THEREFOR

CROSS-REFERENCE TO RELATED APPLICATIONS

This application is a continuation application of International Patent Application No. PCT/CN2012/081013, filed Sep. 5, 2012, which itself claims the priority to Chinese Patent Application Nos. 201110261080.2 and 201210307798.5, filed Sep. 6, 2011 and Aug. 27, 2012, respectively, in the State Intellectual Property Office of P.R. China, which are hereby incorporated herein in their entireties by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates to a method of preparing a substituted phenoxyethyl(isopropyl)acyloxyalkyl phosphonate (phosphate) comprising a phosphorusheterocyclic ring, and its biological activity when used as a herbicide or a fungicide.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the invention.

Phosphonic acid derivatives are a class of compounds with remarkable biological activity. Many phosphonic acid derivatives have been developed as herbicides or plant growth regulators. In the last decade, the inventor has developed over ten classes of phosphonic acid derivatives, which show various herbicidal activity and plant growth regulating activity. For example, class A (Hongwu He et al., Chinese Patent No. ZL97109095.5) and class B (Hongwu He et al., Chinese Patent No. ZL200410012773.8) compounds show various herbicidal activity and plant growth regulating activity.

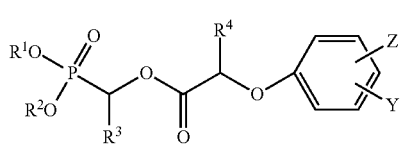

A

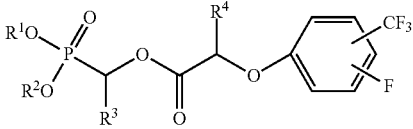

B

SUMMARY OF THE INVENTION

In one aspect, the present invention is directed to a new type of substituted phenoxyethyl(isopropyl)acyloxyalkyl phosphonate (phosphate) compounds comprising a phosphorusheterocyclic ring that has herbicidal activity, and specifically is directed to a new class of phosphonate (phosphate) derivatives that has herbicidal activity and fungicidal (or bactericidal) activity.

In one embodiment, the present invention changes structural skeletons of the class A and B compounds on the basis of the study on the compounds, and provides a class of substituted phenoxyethyl(isopropyl)acyloxyalkyl phosphonate (phosphate) compounds comprising a phosphorusheterocyclic ring, which has a different structure from that of the class A and class B compounds. The substituted phenoxyethyl (isopropyl)acyloxyalkyl phosphonate (phosphate) compound comprising a phosphorusheterocyclic ring has a structural of formula I:

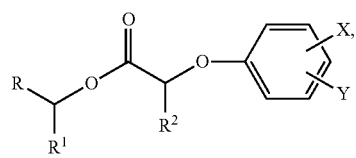

I wherein

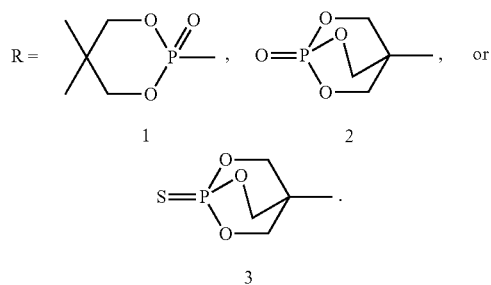

In the general structural formula I, R represents 5,5-dimethyl-1,3,2-dioxaphosphacyclohexan-2-on-2-yl of structure 1, 1-oxo-1-phospha-2,6,7-trioxabicyclo[2,2,2]octan-4-yl of structure 2, or 1-thio-1-phospha-2,6,7-trioxabicyclo[2,2,2]octan-4-yl of structure 3; $R^1$ represents H, $C_1$-$C_4$ alkyl, phenyl, furyl, pyridyl, or phenyl substituted by substituents methyl, methoxyl, nitro, or chloro; $R^2$ represents H or methyl, and when R in the general formula I is a phosphorusheterocyclic ring shown by structure 3, $R^2$ is methyl only; X and Y represent H, halogen, $C_1$-$C_4$ alkyl, or trifluoromethyl, and X and Y are the same or different.

According to certain embodiment of the present invention, a compound characterized by the structure of formula I has a significant inhibitory effect on growth of monocotyledonous or dicotyledonous plants, and can be used as an active ingredient of a herbicide. Specifically, the compound of formula I can be used as an active ingredient of a herbicide for controlling dicotyledonous broadleaf weeds of *Capsella bursa-pastoris, Amaranthus retroflexus, Eclipta prostrata, Abutilon theophrasti* and *Chenopodium serotinum*. A compound of formula I with R characterized by structure 2 has a good inhibitory effect on *Botrytis cinerea*, and can be used as an active ingredient of a fungicide.

In another aspect, the present invention is directed to a method for preparing a substituted phenoxyethyl(isopropyl)acyloxyalkyl phosphonate compound comprising a phosphorusheterocyclic ring represented by general formula I. The method includes reacting a compound represented by general formula II with a compound represented by general formula III below:

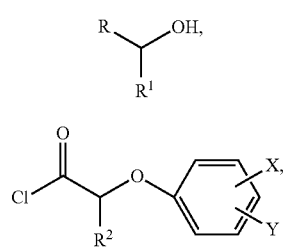

wherein in formula II,

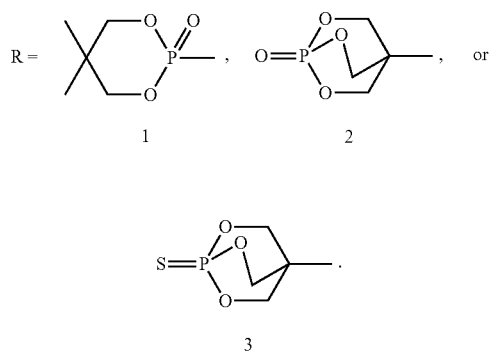

The reaction is represented as follows:

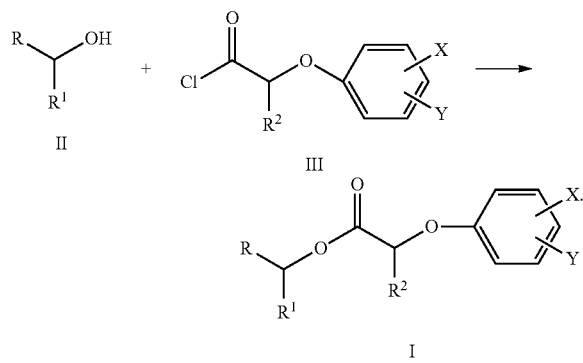

In the above reaction, a molar ratio of a phosphonate (phosphate) compound comprising a phosphorusheterocyclic ring II versus substituted phenoxyacetyl chloride III versus a base is 1:(1.0-2.0):(1.1-3.0). The solvent used is an organic solvent of benzene, chloroform, dichloromethane, dichloroethane, trichloromethane, toluene, acetonitrile, dimethylformamide (DMF), acetone, or ethyl acetate. A high yield can be achieved under the presence of basic catalyst of potassium carbonate, triethylamine, or pyridine, and at a temperature between −20° C. and 110° C. for 2-8 hours (hrs).

These and other aspects of the present invention will become apparent from the following description of the preferred embodiment taken in conjunction with the following drawings, although variations and modifications therein may be effected without departing from the spirit and scope of the novel concepts of the invention.

DETAILED DESCRIPTION OF THE INVENTION

The invention is more particularly described in the following examples that are intended as illustrative only since numerous modifications and variations therein will be apparent to those skilled in the art. Various embodiments of the invention are now described in detail. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terms used in this specification generally have their ordinary meanings in the art, within the context of the invention, and in the specific context where each term is used. Certain terms that are configured to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

As used in the description herein and throughout the claims that follow, the meaning of "a", "an", and "the" includes plural reference unless the context clearly dictates otherwise.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

A method for preparing a compound of formula I of the present invention will be described in detail in the following through embodiments, and the embodiments are not intended to be exhaustive or to limit the invention to the precise forms disclosed. Many modifications and variations are possible in light of the above teaching.

Embodiment 1

Preparation of Compound 1: 2-(2,4-dichlorophenoxyethylacyloxy)(phenyl)methyl-5,5-dimethyl-1,3,2-dioxaphosphorinan-2-one phosphonate

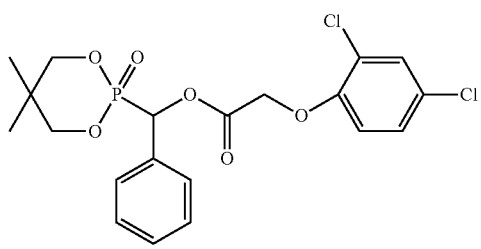 [SMILES: CC1(C)COP(=O)(C(OC(=O)COc2ccc(Cl)cc2Cl)c2ccccc2)OC1]

0.005 mol α-hydroxyalkyl phosphonate and 0.006 mol of potassium carbonate were dissolved in 15 mL benzene and cooled to below 15° C. in an ice-salt bath. Then a 10 mL benzene solution containing 0.0055 mol 2,4-dichlorophenoxyethylacyloxy was added dropwise and slowly to the 15 mL benzene solution. After the addition, the ice bath was removed, and the reaction solution was warmed to room temperature gradually, and refluxed to continue reaction. The reaction was monitored by thin layer chromatography (TLC), and was completed after about 6 hrs. After the reaction was completed, the reaction product was washed with saturated sodium chloride solution until the solution was neutral. After that, the water phase was extracted with an appropriate amount of ethyl acetate twice, and the organic phases were combined. The combined organic phases were dried with anhydrous sodium sulfate overnight. After anhydrous sodium sulfate was filtered off, the solvent was removed from the filtrate to give a crude product. The crude product was recrystallized using petroleum ether and ethanol (petroleum ether:ethanol=2:3 by volume) or purified using column chromatography on silica gel (G-type) with gradient elution (eluent acetone:petroleum ether=1:8 by volume) to give a pure product. The produced pure product was white solid with a yield of 67%, and the melting point (m.p.) was 149.8° C. to 151.2° C.

Element Analysis (%) ($C_{20}H_{21}Cl_2O_6P$):

Calculated value: C, 52.30; H, 4.61.

Measured value: C, 52.79; H, 4.47.

$^1$H NMR (400 MHz, CDCl$_3$): δ 7.43-6.73 (m, 8H), 6.36 (d, J=12.0 Hz, 1H), 4.82 (s, 2H), 4.07-4.04 (m, 4H), 1.16 (s, 3H), 0.90 (s, 3H).

$^{31}$P NMR (160 MHz, CDCl$_3$): δ 7.2.

EI-MS m/z (%): 458 (M$^+$+1, 13), 311 (9), 245 (11), 229 (28), 177 (43), 175 (77), 162 (11), 147 (16), 137 (15), 136 (26), 135 (90), 121 (100), 90 (90).

IR (KBr): ν 3092, 2963, 1770, 1485, 1274, 1193, 1072, 1070, 864, 800 cm$^{-1}$.

Compounds 2-8 were prepared by using a method similar to that of compound 1, with data of structural identification as follows:

Compound 2: 2-(2,4-dichlorophenoxyethylacyloxy)(2-chlorophenyl)methyl-5,5-dimethyl-1,3,2-dioxaphosphorinan-2-one phosphonate

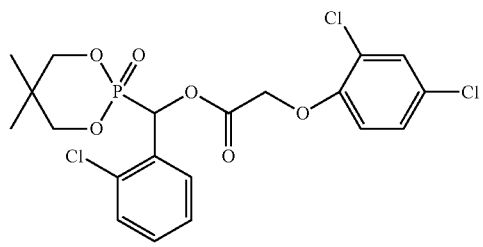 [SMILES: CC1(C)COP(=O)(C(OC(=O)COc2ccc(Cl)cc2Cl)c2ccccc2Cl)OC1]

The resulting pure product was white solid with a yield of 70%, and the m.p. was 118.0 to 120.3° C.

Element Analysis (%) ($C_{20}H_{20}Cl_3O_6P$):

Calculated value: C, 48.66; H, 4.08.

Measured value: C, 48.79; H, 3.93.

$^1$H NMR (400 MHz, CDCl$_3$): δ 7.70-6.94 (m, 7H), 6.75-6.72 (d, J=8.8 Hz, 1H, PCHO), 4.83 (d, J=6.0 Hz, 2H, OCH$_2$CO), 4.20-4.00 (m, 4H, 2×(OCH$_2$)), 1.22 (s, 3H), 0.93 (s, 3H).

IR (KBr): ν 3102, 2975, 1765, 1481, 1283, 1180, 1061, 1011, 836, 813 cm$^{-1}$.

Compound 3: 2-(2,4-dichlorophenoxyethylacyloxy)(4-chlorophenyl)methyl-5,5-dimethyl-1,3,2-dioxaphosphorinan-2-one phosphonate

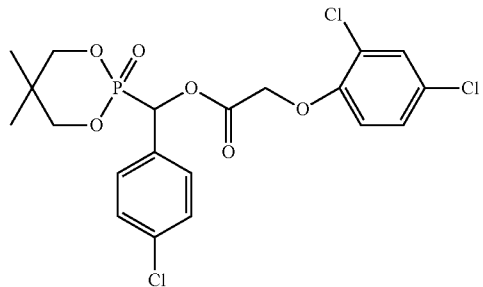 [SMILES: CC1(C)COP(=O)(C(OC(=O)COc2ccc(Cl)cc2Cl)c2ccc(Cl)cc2)OC1]

The resulting pure product was white solid, with a yield of 71%, the m.p. was 120.1 to 120.5° C.

Element Analysis (%) ($C_{20}H_{20}Cl_3O_6P$):

Calculated value: C, 48.66; H, 4.08.

Measured value: C, 48.89; H, 3.83.

$^1$H NMR (400 MHz, CDCl$_3$): δ 7.41-6.72 (m, 7H), 6.32-6.29 (d, J=12.4 Hz, 1H, PCHO), 4.80 (s, 2H, OCH$_2$CO), 4.10-3.91 (m, 4H, 2×(OCH$_2$)), 1.16 (s, 3H), 0.92 (s, 3H).

$^{31}$P NMR (160 MHz, CDCl$_3$): δ 7.48.

IR (KBr): ν 3090, 2978, 1768, 1484, 1273, 1189, 1073, 1020, 830, 815 cm$^{-1}$.

Compound 4: 2-(2,4-dichlorophenoxyethylacyloxy)(2,4-dichlorophenyl)methyl-5,5-dimethyl-1,3,2-dioxaphosphorinan-2-one phosphonate

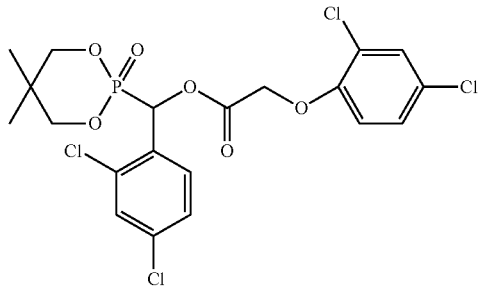 [SMILES: CC1(C)COP(=O)(C(OC(=O)COc2ccc(Cl)cc2Cl)c2ccc(Cl)cc2Cl)OC1]

The resulting pure product was white solid with a yield of 65%, and the m.p. was 169.8 to 170.1° C.

Element Analysis (%) ($C_{20}H_{19}Cl_4O_6P$):

Calculated value: C, 45.48; H, 3.63.

Measured value: C, 45.94; H, 3.44.

$^1$H NMR (400 MHz, $CDCl_3$): δ 7.63-6.82 (m, 6H), 6.75-6.72 (d, J=8.8 Hz, 1H, PCHO), 4.81 (d, J=4.0 Hz, 2H, $OCH_2CO$), 4.17-4.01 (m, 4H), 1.21 (s, 3H), 0.95 (s, 3H).

$^{31}$P NMR (160 MHz, $CDCl_3$): δ 5.84.

IR (KBr): ν 3102, 2974, 1772, 1480, 1288, 1179, 1057, 1006, 840, 813 $cm^{-1}$.

Compound 5: 2-(2,4-dichlorophenoxyethylacyloxy)(3,4-dichlorophenyl)methyl-5,5-dimethyl-1,3,2-dioxaphosphorinan-2-one phosphonate

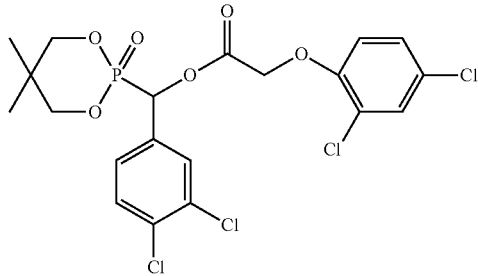 [SMILES: CC1(C)COP(=O)(C(OC(=O)COc2ccc(Cl)cc2Cl)c2ccc(Cl)c(Cl)c2)OC1]

The resulting pure product was white solid with a yield of 72%, and the m.p. was 107.0 to 108.0° C.

Element Analysis (%) ($C_{20}H_{19}Cl_4O_6P$):

Calculated value: C, 45.48; H, 3.63.

Measured value: C, 45.62; H, 3.88.

$^1$H NMR (400 MHz, $CDCl_3$): δ 7.47-6.72 (m, 6H), 6.26 (d, J=12.8 Hz, 1H), 4.82 (d, J=6.4 Hz, 2H), 4.14-4.03 (m, 4H), 1.17 (s, 3H), 0.97 (s, 3H).

IR (KBr): ν 3090, 2966, 1761, 1478, 1279, 1189, 1057, 1007, 836, 804 $cm^{-1}$.

Compound 6: 2-(2,4-dichlorophenoxyethylacyloxy)(4-methoxyphenyl)methyl-5,5-dimethyl-1,3,2-dioxaphosphorinan-2-one phosphonate

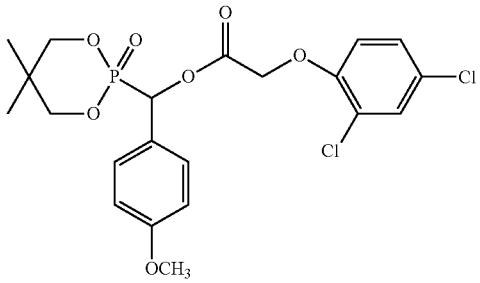 [SMILES: COc1ccc(C(OC(=O)COc2ccc(Cl)cc2Cl)P2(=O)OCC(C)(C)CO2)cc1]

The resulting pure product was white solid with a yield of 77%, and the m.p. was 120.3 to 123.6° C.

Element Analysis (%) ($C_{21}H_{23}Cl_2O_7P$):

Calculated value: C, 51.55; H, 4.74.

Measured value: C, 52.03; H, 4.34.

$^1$H NMR (400 MHz, $CDCl_3$): δ 7.41-6.72 (m, 7H), 6.32 (d, J=12.0 Hz, 1H), 4.80 (s, 2H), 4.10-3.92 (m, 4H), 1.16 (s, 3H), 0.92 (s, 3H).

IR (KBr): ν 3090, 2978, 1768, 1484, 1273, 1190, 1073, 1020, 815 $cm^{-1}$.

Compound 7: 2-(2,4-dichlorophenoxyethylacyloxy)(4-methylphenyl)methyl-5,5-dimethyl-1,3,2-dioxaphosphorinan-2-one phosphonate

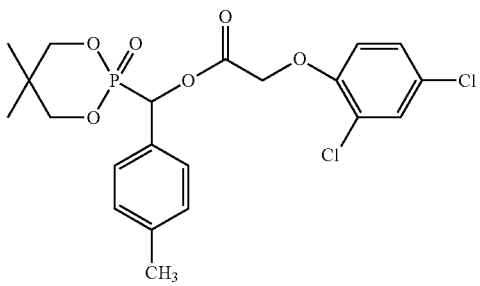 [SMILES: Cc1ccc(C(OC(=O)COc2ccc(Cl)cc2Cl)P2(=O)OCC(C)(C)CO2)cc1]

The resulting pure product was white solid with a yield of 87%, and the m.p. was 106.2 to 108.1° C.

Element Analysis (%) ($C_{21}H_{23}Cl_2O_6P$):

Calculated value: C, 53.29; H, 4.90.

Measured value: C, 52.75; H, 4.28.

$^1$H NMR (400 MHz, $CDCl_3$): δ 7.41-6.71 (m, 7H), 6.31 (d, J=11.2 Hz, 1H), 4.79 (s, 2H), 4.11-3.92 (m, 4H), 1.16 (s, 3H), 0.93 (s, 3H).

IR (KBr): ν 3097, 2978, 1756, 1483, 1289, 1198, 1055, 1006, 837 $cm^{-1}$.

Compound 8: 2-(2,4-dichlorophenoxyethylacyloxy) (4-nitrophenyl)methyl-5,5-dimethyl-1,3,2-dioxaphosphorinan-2-one phosphonate

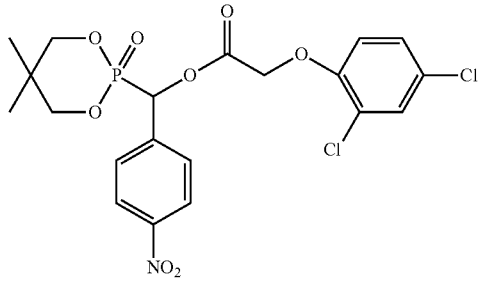

The resulting pure product was white solid with a yield of 73%, and the m.p. was 123.9 to 125.5° C.

Element Analysis (%) ($C_{20}H_{20}Cl_2NO_8P$):
Calculated value: C, 47.64; H, 4.00.
Measured value: C, 47.81; H, 4.06.

$^1$H NMR (400 MHz, CDCl$_3$): δ 8.24-6.76 (m, 7H), 6.42 (d, J=13.6 Hz, 1H), 4.85 (d, J=4.0 Hz, 2H), 4.18-4.02 (m, 4H), 1.27 (s, 3H), 0.96 (s, 3H).

IR (KBr): ν 3042, 2970, 1775, 1521, 1480, 1350, 1275, 1187, 1060, 1008, 867, 802 cm'.

Embodiment 2

Preparation of Compound 9: 2-(2,4-dichlorophenoxyethylacyloxy)(2-pyridyl)methyl-5,5-dimethyl-1,3,2-dioxaphosphorinan-2-one phosphonate

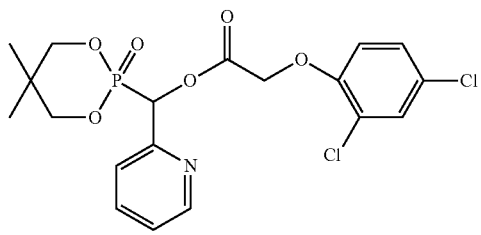 [SMILES: CC1(C)COP(=O)(C(OC(=O)COc2ccc(Cl)cc2Cl)c2ccccn2)OC1]

0.005 mol of α-hydroxyalkyl phosphonate, 0.006 mol of pyridine and 15 mL of DMF were cooled to below 15° C. on in an ice-salt bath, and 10 mL of DMF solution containing 0.0055 mol of 2,4-dichlorophenoxyacetyl chloride was added dropwise slowly. After the addition, the ice bath was removed, and the reaction solution was warmed to room temperature gradually, and refluxed at 80° C. to continue reaction. The reaction was monitored by TLC, and was completed after about 4 hrs. After the reaction was completed, the mixture was washed with saturated aqueous sodium chloride until the solution was neutral. The water phase was extracted with ethyl acetate twice, and the organic phases were combined. The mixture was dried with anhydrous sodium sulfate overnight, and after anhydrous sodium sulfate was filtered off, the solvent was removed from the filtrate to give a crude product. The crude product was recrystallized from petroleum ether and ethanol (petroleum ether:ethanol=2:3 by volume) or purified by column chromatography on silica gel (G-type) with gradient elution (eluent acetone: petroleum ether=1:8 by volume) to give a pure product.

The resulting pure product was white solid, with a yield of 65%, and the m.p. was 34.0 to 36.0° C.

Element Analysis (%) ($C_{19}H_{20}Cl_2NO_6P$):
Calculated value: C, 49.58; H, 4.38.
Measured value: C, 49.80; H, 4.14.

$^1$H NMR (400 MHz, CDCl$_3$): δ 8.62-6.92 (m, 7H), 6.52 (d, J=12.4 Hz, 1H), 4.93 (d, J=4.0 Hz, 2H), 4.30-3.95 (m, 4H), 1.21 (s, 3H), 0.92 (s, 3H).

IR (KBr): ν 3055, 2969, 1775, 1485, 1290, 1177, 1059, 990, 848, 807 cm$^{-1}$.

Compounds 10-21 were prepared by using a method similar to that of compound 9, with data of structural identification as follows:

Compound 10: 2-(2,4-dichlorophenoxyethylacyloxy)(2-furyl)methyl-5,5-dimethyl-1,3,2-dioxaphosphorinan-2-one phosphonate

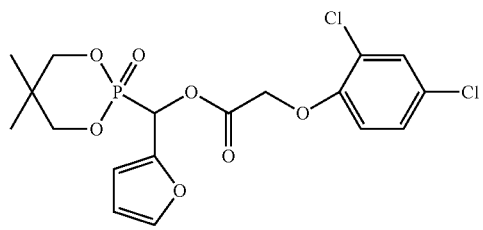 [SMILES: CC1(C)COP(=O)(C(OC(=O)COc2ccc(Cl)cc2Cl)c2ccco2)OC1]

The resulting pure product was white solid, with a yield of 72%, and the m.p. was 109.8 to 113.6° C.

Element Analysis (%) ($C_{18}H_{19}Cl_2O_7P$):
Calculated value: C, 48.13; H, 4.26.
Measured value: C, 48.67; H, 3.87.

$^1$H NMR (400 MHz, CDCl$_3$): δ 7.47-6.42 (m, 6H), 6.42 (s, 1H), 4.79 (s, 2H), 4.14-4.05 (m, 4H, 2×(OCH$_2$)), 1.23 (s, 3H), 0.94 (s, 3H).

EI-MS m/z (%): 449 (M$^+$1), 245 (25), 229 (40), 175 (29), 147 (21), 133 (70), 111 (22), 95 (34), 81 (41), 69 (100).

IR (KBr): ν 3114, 2966, 1769, 1483, 1282, 1194, 1072, 1009, 857, 805 cm$^{-1}$.

Compound 11: 2-(2,4-dichlorophenoxyethylacyloxy)(methyl)methyl-5,5-dimethyl-1,3,2-dioxaphosphorinan-2-one phosphonate

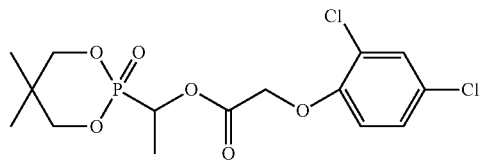 [SMILES: CC(OC(=O)COc1ccc(Cl)cc1Cl)P1(=O)OCC(C)(C)CO1]

The resulting pure product was white solid with a yield of 64%, and the m.p. was 62.1 to 63.8° C.

Element Analysis (%) ($C_{15}H_{19}Cl_2O_6P$):
Calculated value: C, 45.36; H, 4.82.
Measured value: C, 45.11; H, 4.89.

$^1$H NMR (400 MHz, CDCl$_3$): δ 7.41-6.78 (m, 3H), 5.50 (m, 1H, PCHO), 4.76 (d, J=4.0 Hz, 2H, —OCH$_2$CO—), 4.15-3.92 (m, 4H, 2×(OCH$_2$)), 1.61-1.59 (m, 3H), 1.16 (s, 3H), 1.00 (s, 3H).

EI-MS m/z (%): 397 (M$^+$ 6), 178 (30), 133 (32), 111 (39), 95 (14), 69 (100).

Compound 12: 2-(2,4-dichlorophenoxyethylacyloxy)(isopropyl)methyl-5,5-dimethyl-1,3,2-dioxaphosphorinan-2-one phosphonate

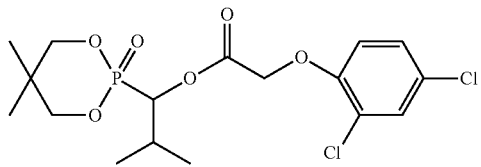 [SMILES: CC(C)C(OC(=O)COc1ccc(Cl)cc1Cl)P1(=O)OCC(C)(C)CO1]

The resulting pure product was white solid, with a yield of 86%, and the m.p. was 120.2 to 121.1° C.

Element Analysis (%) ($C_{17}H_{23}Cl_2O_6P$):

Calculated value: C, 48.02; H, 5.45.

Measured value: C, 48.26; H, 5.04.

$^1$H NMR (400 MHz, CDCl$_3$): δ 7.42-7.41 (d, 1H, J=2.4 Hz, 3-phenyl-H), 7.19-7.16 (dd, 1H, J=2.4 Hz, J=2.4 Hz, 5-phenyl-H), 6.79-6.76 (d, 1H, J=8.8 Hz, 6-phenyl-H), 5.31-5.27 (t, 1H, J=7.2 Hz, PCHO), 4.81-4.79 (d, J=4.8 Hz, 2H, OCH$_2$CO), 4.15-3.92 (m, 4H, 2×(OCH$_2$)), 2.37-2.33 (m, 1H), 1.15 (s, 3H), 1.13-1.01 (m, 6H), 0.99 (s, 3H).

IR (KBr): 3076, 2971, 1759, 1480, 1282, 1205, 1057, 1012, 834, 808 cm$^{-1}$.

Compound 13: 2-(2,4-dichlorophenoxyethylacyloxy)(butyl)methyl-5,5-dimethyl-1,3,2-dioxaphosphorinan-2-one phosphonate

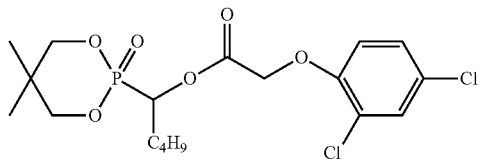

The resulting pure product was white solid, with a yield of 72%, and the m.p. was 75.2-76.1° C.

Element Analysis (%) ($C_{18}H_{25}Cl_2O_6P$):

Calculated value: C, 49.22; H, 5.74.

Measured value: C, 49.55; H, 5.39.

$^1$H NMR (400 MHz, CDCl$_3$): δ 7.41-7.40 (d, 1H, J=2.4 Hz, 3-phenyl-H), 7.19-7.16 (dd, 1H, J=2.4 Hz, J=2.4 Hz, 5-phenyl-H), 6.79-6.76 (d, 1H, J=8.8 Hz, 6-phenyl-H), 5.50-5.47 (d, 1H, J=6.0 Hz, PCHO), 4.78-4.69 (s, 2H, OCH$_2$CO), 4.16-3.91 (m, 4H, 2×(OCH$_2$)), 1.94-1.93 (m, 2H), 1.35-1.31 (m, 4H) 1.15 (s, 3H), 1.02 (s, 3H), 0.91-0.86 (m, 3H).

IR (KBr): ν 3070, 2953, 1755, 1478, 1281, 1198, 1068, 1009, 838, 799 cm$^{-1}$.

Compound 14: 2-(phenoxyethylacyloxy)(2-furyl)methyl-5,5-dimethyl-1,3,2-dioxaphosphorinan-2-one phosphonate

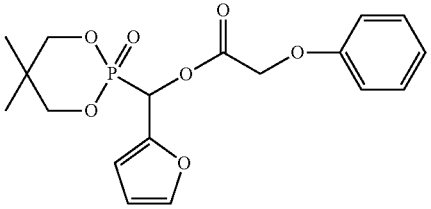 [SMILES: CC1(C)COP(=O)(C(OC(=O)COc2ccccc2)c2ccco2)OC1]

The resulting pure product was faint yellow liquid, with a yield of 78%, and n$_D^{20}$ was 1.5169.

Element Analysis (%) ($C_{18}H_{21}O_7P$):

Calculated value: C, 56.84; H, 5.57.

Measured value: C, 56.70; H, 5.18.

$^1$H NMR (400 MHz, CDCl$_3$): δ 7.48-6.72 (m, 7H, —C$_6$H$_5$, 5- and 4-furyl-H), 6.55-6.51 (d, J=14.4 Hz, PCHO), 6.42 (s, 1H, 3-furyl-H), 4.74 (s, 2H, OCH$_2$CO), 4.19-4.04 (m, 4H, 2×(OCH$_2$)), 1.24 (s, 3H), 0.93 (s, 3H).

EI-MS m/z (%): 380 (M$^+$, 7), 245 (15), 229 (28), 175 (5), 133 (59), 107 (80), 81 (37), 79 (42), 77 (100), 69 (83).

IR (KBr): ν 3060, 2970, 1744, 1600, 1494, 1264, 1174, 1060, 1009, 833 cm$^{-1}$.

Compound 15: 2-(2-chlorophenoxyethylacyloxy)(2-furyl)methyl-5,5-dimethyl-1,3,2-dioxaphosphorinan-2-one phosphonate

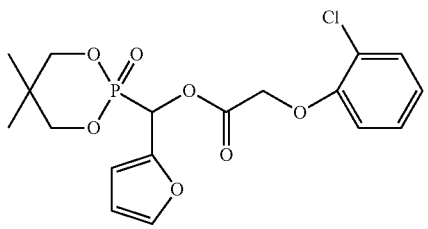 [SMILES: CC1(C)COP(=O)(C(OC(=O)COc2ccccc2Cl)c2ccco2)OC1]

The resulting pure product was faint yellow liquid, with a yield of 82%, and n$_D^{20}$ was 1.5211.

Element Analysis (%) ($C_{18}H_{20}ClO_7P$):

Calculated value: C, 52.12; H, 4.86.

Measured value: C, 52.33; H, 4.52.

$^1$H NMR (400 MHz, CDCl$_3$): δ 7.48-6.53 (m, 6H, C$_6$H$_4$, 5- and 4-furyl-H), 6.50-6.46 (d, 1H, J=14.4 Hz, PCHO), 6.42 (s, 1H, 3-furyl-H), 4.71 (s, 2H, OCH$_2$CO), 4.12-4.05 (m, 4H, 2×(OCH$_2$)), 1.23 (s, 3H), 0.94 (s, 3H).

EI-MS m/z (%): 414 (M$^+$, 3), 245 (30), 229 (17), 141 (37), 133 (75), 113 (35), 95 (32), 81 (45), 69 (100).

IR (KBr): ν 3124, 2971, 1765, 1596, 1492, 1291, 1170, 1061, 1011, 826 cm$^{-1}$.

Compound 16: 2-(2-fluorphenoxyethylacyloxy)(2-furyl)methyl-5,5-dimethyl-1,3,2-dioxaphosphorinan-2-one phosphonate

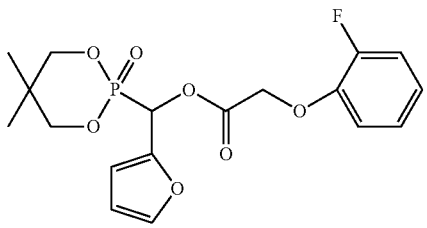

The resulting pure product was faint yellow liquid, with a yield of 75%, and $n_D^{20}$ was 1.5051.
Element Analysis (%) ($C_{18}H_{20}FO_7P$):
Calculated value: C, 54.28; H, 5.06.
Measured value: C, 53.89; H, 4.73.
$^1$H NMR (400 MHz, CDCl$_3$): δ 7.47-6.70 (m, 5H, —C$_6$H$_4$, 5- and 4-furyl-H), 6.53-6.49 (d, J=14.4 Hz, PCHO), 6.42 (s, 1H, 3-furyl-H), 4.79 (s, 2H, OCH$_2$CO), 4.25-4.05 (m, 4H, 2×(OCH$_2$)), 1.28 (s, 3H), 0.93 (s, 3H).
IR (KBr): ν 3124, 2973, 1765, 1506, 1288, 1173, 1062, 1012, 831 cm$^{-1}$.

Compound 17: 2-(3-methylphenoxyethylacyloxy)(2-furyl)methyl-5,5-dimethyl-1,3,2-dioxaphosphorinan-2-one phosphonate

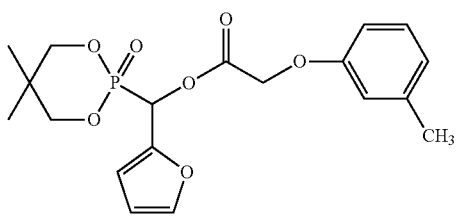

The resulting pure product was faint yellow liquid, with a yield of 74%, and the $n_D^{20}$ was 1.5125.
Element Analysis (%) ($C_{19}H_{23}O_7P$):
Calculated value: C, 57.87; H, 5.88.
Measured value: C, 57.86; H, 5.85.
$^1$H NMR (400 MHz, CDCl$_3$): δ 7.48-6.50 (m, 7H), 6.42 (s, 1H), 4.72 (s, 2H), 4.22-3.99 (m, 4H), 2.31 (s, 3H), 1.24 (s, 3H), 0.94 (s, 3H).
IR (KBr): ν 3037, 2971, 1765, 1606, 1491, 1292, 1154, 1062, 1012, 866 cm$^{-1}$.

Compound 18: 2-(3-trifluormethylphenoxyethylacyloxy)(2-furyl)methyl-5,5-dimethyl-1,3,2-dioxaphosphorinan-2-one phosphonate

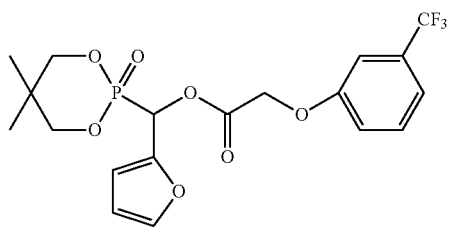 [SMILES: CC1(C)COP(=O)(C(OC(=O)COc2cccc(C(F)(F)F)c2)c2ccco2)OC1]

The resulting pure product was faint yellow liquid, with a yield of 75%, and $n_D^{20}$ was 1.5612.
Element Analysis (%) ($C_{19}H_{20}F_3O_7P$):
Calculated value: C, 50.90; H, 4.50.
Measured value: C, 49.40; H, 4.16.
$^1$H NMR (400 MHz, CDCl$_3$): δ 7.46 (s, 1H, 5-furyl-H), 7.32-6.70 (m, 5H, phenyl-H, 4-furyl-H), 6.53-6.49 (d, 1H, J=13.2 Hz, PCHO), 6.42 (s, 1H, 3-furyl-H), 4.78 (s, 2H, OCH$_2$CO), 4.20-4.01 (m, 4H, 2×(OCH$_2$)), 1.22 (s, 3H), 0.92 (s, 3H).
EI-MS m/z (%): 448 (M$^+$, 3), 245 (38), 229 (15), 175 (54), 145 (67), 133 (93), 127 (21), 96 (19), 81 (47), 69 (100).
IR (KBr): ν 2972, 1742, 1596, 1492, 1261, 1170, 1062, 1008, 827 cm$^{-1}$.

Compound 19: 2-(4-tert-butylphenoxyethylacyloxy)(2-furyl)methyl-5,5-dimethyl-1,3,2-dioxaphosphorinan-2-one phosphonate

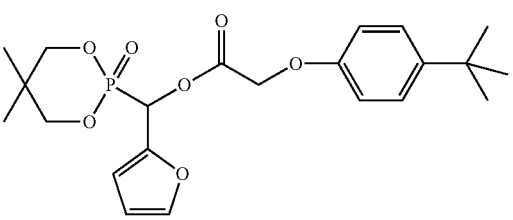 [SMILES: CC1(C)COP(=O)(C(OC(=O)COc2ccc(C(C)(C)C)cc2)c2ccco2)OC1]

The resulting pure product was faint yellow liquid, with a yield of 65%, and the $n_D^{20}$ was 1.4790.
Element Analysis (%) ($C_{20}H_{21}Cl_2O_6P$):
Calculated value: C, 52.30; H, 4.61.
Measured value: C, 51.64; H, 4.95.
$^1$H NMR (400 MHz, CDCl$_3$): δ 7.47-6.41 (m, 7H), 6.41 (s, 1H), 4.71 (s, 2H), 4.07-4.03 (m, 4H), 1.21-1.28 (m, 9H), 1.28 (s, 3H), 0.92 (s, 3H).
IR (KBr): ν 3123, 2965, 1771, 1611, 1513, 1475, 1291, 1169, 1062, 1011, 830 cm$^{-1}$.

Compound 20: 2-(4-chlorophenoxyethylacyloxy)(2-furyl)methyl-5,5-dimethyl-1,3,2-dioxaphosphorinan-2-one phosphonate

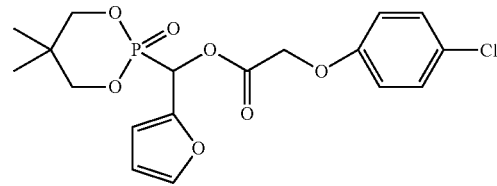 [SMILES: CC1(C)COP(=O)(C(OC(=O)COc2ccc(Cl)cc2)c2ccco2)OC1]

The resulting pure product was faint yellow liquid, with a yield of 80% and $n_D^{20}$ was 1.5213.
Element Analysis (%) ($C_{18}H_{20}ClO_7P$):
Calculated value: C, 52.12; H, 4.86.
Measured value: C, 52.46; H, 5.38.
$^1$H NMR (400 MHz, CDCl$_3$): δ 7.47 (s, 1H, 5-furyl-H), 7.23-7.22 (d, 2H, J=2.4 Hz, 3- and 5-phenyl-H), 6.82-6.79 (d, 2H, J=9.6 Hz, 2 and 6-phenyl-H), 6.72 (s, 1H, 4-furyl-H), 6.52-6.48 (d, 1H, J=13.2 Hz, PCHO), 6.42 (s, 1H, 3-furyl-H), 4.76 (s, 2H, OCH$_2$CO), 4.14-4.02 (m, 4H, 2×(OCH$_2$)), 1.22 (s, 3H), 0.94 (s, 3H).
EI-MS m/z (%): 414 (M$^+$, 2), 245 (12), 229 (39), 175 (5), 141 (21), 133 (63), 111 (14), 95 (35), 81 (50), 69 (100).
IR (KBr): ν 3125, 2970, 1766, 1595, 1492, 1291, 1170, 1062, 1011, 826 cm$^{-1}$.

Compound 21: 2-(2-methyl-4-chlorophenoxyethylacyloxy)(2-furyl)methyl-5,5-dimethyl-1,3,2-dioxaphosphorinan-2-one phosphonate

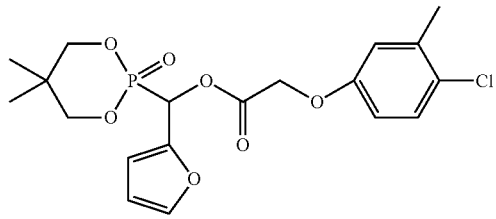 [SMILES: Cc1cc(OCC(=O)OC(c2ccco2)P2(=O)OCC(C)(C)CO2)ccc1Cl]

The resulting pure product was faint yellow liquid, with a yield of 82%, and $n_D^{20}$ 1.5230.

Element Analysis (%) ($C_{19}H_{22}ClO_7P$):
Calculated value: C, 53.22; H, 5.17.
Measured value: C, 53.95, H, 6.15.

$^1$H NMR (400 MHz, $CDCl_3$): δ 7.47 (s, 1H, 5-furyl-H), 7.24-6.69 (m, 4H, 2, 5- and 6-phenyl-H, 4-furyl-H), 6.52-6.48 (d, 1H, J=14.4 Hz, PCHO), 6.42 (s, 1H, 3-furyl-H), 4.70 (s, 2H), 4.16-4.03 (m, 4H), 2.32 (s, 3H), 1.23 (s, 3H), 0.96 (s, 3H).

IR (KBr): ν 3124, 2968, 1770, 1600, 1482, 1291, 1166, 1062, 1012, 828 $cm^{-1}$.

Embodiment 3

Preparation of compound 22 2-(phenoxyethylacyloxy)(phenyl)methyl-5,5-dimethyl-1,3,2-dioxaphosphorinan-2-one phosphonate

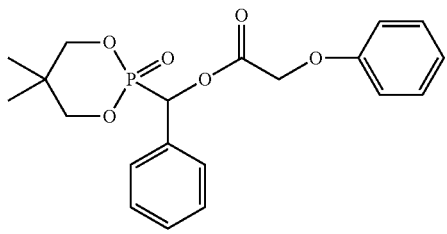 [SMILES: CC1(C)COP(=O)(C(OC(=O)COc2ccccc2)c2ccccc2)OC1]

0.003 mol of α-hydroxyalkyl phosphonate, 0.0036 mol of pyridine and 15 mL of toluene were cooled to below 15° C. in an ice-salt bath, and 10 mL of toluene solution containing 0.0036 mol of 2,4-dichlorophenoxyacetyl chloride was added dropwise slowly. After the addition, the ice bath was removed, and the reaction solution was warmed to room temperature gradually, and refluxed at 110° C. to continue reaction. The reaction was monitored by TLC, and was completed after about 3 hrs. After the reaction was completed, the solvent was removed directly under a reduced pressure, and the residue was washed with 20 mL of water. Then, the water phase was extracted with ethyl acetate twice, and the organic phases were combined. The mixture was dried with anhydrous sodium sulfate overnight, and after anhydrous sodium sulfate was filtered off, the solvent was removed from the filtrate to give a crude product. The crude product was recrystallized from petroleum ether and ethanol (petroleum ether:ethanol=2:3 by volume) or purified by column chromatography on silica gel (G-type) with gradient elution (eluent acetone:petroleum ether=1:8 by volume) to give a pure product.

The resulting pure product was faint yellow solid, with a yield of 80%, and the m.p. was 80.4 to 81.3° C.

Element Analysis (%) ($C_{19}H_{22}O_6P$):
Calculated value: C, 60.48; H, 5.88.
Measured value: C, 61.15; H, 5.68.

$^1$H NMR (400 MHz, $CDCl_3$): δ 7.44-6.87 (m, 10H), 6.38-6.34 (d, 1H, J=12.0 Hz, PCHO), 4.77-4.76 (d, 2H, J=3.6 Hz, $OCH_2CO$), 4.13-3.98 (m, 4H, 2×($OCH_2$)), 1.17 (s, 3H), 0.91 (s, 3H).

EI-MS m/z (%): 390 ($M^+$, 1), 240 (28), 133 (59), 107 (58), 105 (30), 79 (29), 77 (100), 69 (70).

IR (KBr): ν 3064, 2971, 1765, 1598, 1492, 1290, 1194, 1054, 1004, 830 $cm^{-1}$.

Compounds 23-30 and Compounds 84-85 were prepared by using a method similar to that of compound 22, with data of structural identification as follows:

Compound 23: 2-(2-chlorophenoxyethylacyloxy)(phenyl)methyl-5,5-dimethyl-1,3,2-dioxaphosphorinan-2-one phosphonate

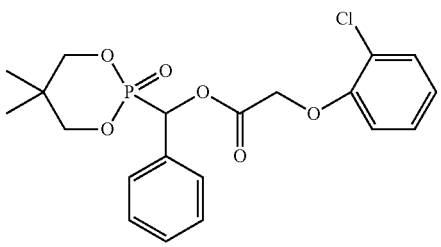 [SMILES: CC1(C)COP(=O)(C(OC(=O)COc2ccccc2Cl)c2ccccc2)OC1]

The resulting pure product was faint yellow solid, with a yield of 82%, and the m.p. was 87.8 to 88.2° C.

Element Analysis (%) ($C_{20}H_{22}ClO_6P$):
Calculated value: C, 56.55; H, 5.22.
Measured value: C, 56.74; H, 5.46.

$^1$H NMR (400 MHz, $CDCl_3$): δ 7.43-6.79 (m, 9H), 6.38-6.35 (d, 1H, J=12.4 Hz, PCHO), 4.84 (s, 2H, $OCH_2CO$), 4.16-3.96 (m, 4H, 2×($OCH_2$)), 1.17 (s, 3H), 0.90 (s, 3H).

EI-MS m/z (%): 424 ($M^+$, 3), 240 (22), 141 (34), 133 (86), 105 (45), 91 (14), 77 (51), 69 (100).

IR (KBr): ν 3014, 2968, 1752, 1590, 1493, 1293, 1190, 1056, 837 $cm^{-1}$.

Compound 24: 2-(2-fluorphenoxyethylacyloxy)(phenyl)methyl-5,5-dimethyl-1,3,2-dioxaphosphorinan-2-one phosphonate

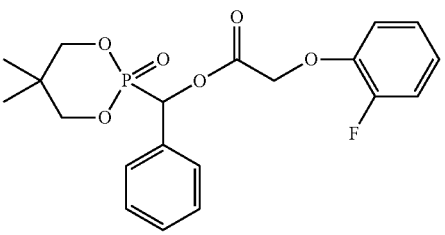 [SMILES: CC1(C)COP(=O)(C(OC(=O)COc2ccccc2F)c2ccccc2)OC1]

The resulting pure product was faint yellow solid, with a yield of 77%, and the m.p. was 69.9 to 71.2° C.

Element Analysis (%) ($C_{20}H_{22}FO_6P$):
Calculated value: C, 58.82; H, 5.43.
Measured value: C, 58.81; H, 5.15.

¹H NMR (400 MHz, CDCl₃): δ 7.44-6.89 (m, 9H), 6.36 (d, 1H, J=12.4 Hz, PCHO), 4.83 (d, 2H, J=3.6 Hz, OCH₂CO), 4.16-4.04 (m, 4H, 2×(OCH₂)), 1.18 (s, 3H), 0.91 (s, 3H); EI-MS m/z (%): 408 (M⁺, 1), 240 (72), 177 (7), 133 (100), 125 (49), 95 (34), 69 (56).

IR (KBr): ν 3068, 2972, 1751, 1613, 1505, 1291, 1190, 1055, 1005, 836 cm⁻¹.

Compound 25: 2-(3-methylphenoxyethylacyloxy)(phenyl)methyl-5,5-dimethyl-1,3,2-dioxaphosphorinan-2-one phosphonate

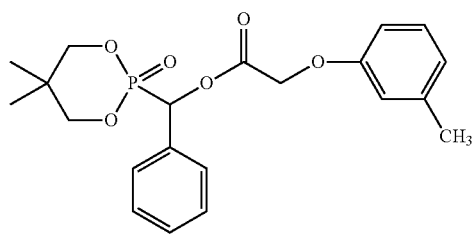

The resulting pure product was white solid, with a yield of 74%, and the m.p. was 75.5 to 76.6° C.
Element Analysis (%) (C₂₁H₂₅O₆P):
Calculated value: C, 62.37; H, 6.23.
Measured value: C, 62.08; H, 6.18.
¹H NMR (400 MHz, CDCl₃): δ 8.03-6.67 (m, 9H), 6.35 (d, J=12.0 Hz, 1H), 4.75 (d, J=3.2 Hz, 2H), 4.12-4.00 (m, 4H), 2.96 (s, 3H), 1.16 (s, 3H), 0.87 (s, 3H).
IR (KBr): ν 3059, 2970, 1777, 1604, 1492, 1276, 1174, 1069, 1003, 835 cm⁻¹.

Compound 26: 2-(3-trifluormethylphenoxyethylacyloxy)(phenyl)methyl-5,5-dimethyl-1,3,2-dioxaphosphorinan-2-one phosphonate

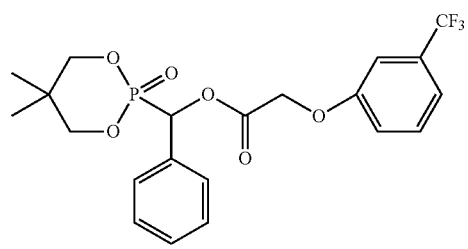 [SMILES: CC1(C)COP(=O)(C(OC(=O)COc2cccc(C(F)(F)F)c2)c2ccccc2)OC1]

The resulting pure product was white solid, with a yield of 75%, and the m.p. was 101.6 to 102.4° C.
Element Analysis (%) (C₂₁H₂₂F₃O₆P):
Calculated value: C, 55.03; H, 4.84.
Measured value: C, 55.35; H, 4.55.
¹H NMR (400 MHz, CDCl₃): δ 7.45-7.05 (m, 9H), 6.37 (d, 1H, J=12.8 Hz, PCHO), 4.81 (d, 2H, J=4.8 Hz, OCH₂CO), 4.09-3.94 (m, 4H, 2×(OCH₂)), 1.26 (s, 3H), 0.92 (s, 3H).
EI-MS m/z (%): 458 (M⁺, 4), 239 (4), 200 (100), 167 (6), 155 (55), 125 (99), 101 (34), 89 (84).
IR (KBr): ν 3066, 2972, 1594, 1494, 1771, 1288, 1171, 1063, 1012, 836 cm⁻¹.

Compound 27: 2-(4-tert-butylphenoxyethylacyloxy)(phenyl)methyl-5,5-dimethyl-1,3,2-dioxaphosphorinan-2-one phosphonate

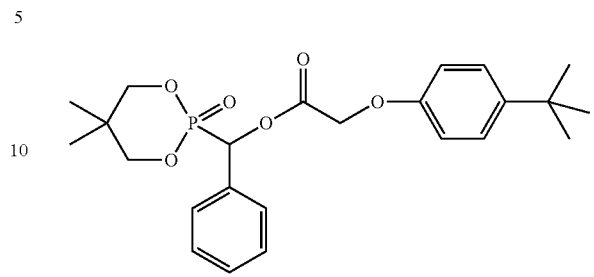

The resulting pure product was faint yellow liquid, with a yield of 86.5%, and $n_D^{20}$ was 1.5121.
Element Analysis (%) (C₂₄H₃₁O₆P):
Calculated value: C, 64.56; H, 7.00.
Measured value: C, 64.00; H, 7.22.
¹H NMR (400 MHz, CDCl₃): δ 7.54-7.29 (m, 9H), 6.81 (d, J=2.4 Hz, 1H), 4.75 (d, J=4.0 Hz, 1H), 4.17-4.02 (m, 4H), 1.25-1.22 (m, 9H), 1.18 (s, 3H), 0.94 (s, 3H);
IR (KBr): ν 3064, 2966, 1769, 1613, 1513, 1283, 1173, 1060, 1011, 834 cm⁻¹.

Compound 28: 2-(4-chlorophenoxyethylacyloxy)(phenyl)methyl-5,5-dimethyl-1,3,2-dioxaphosphorinan-2-one phosphonate

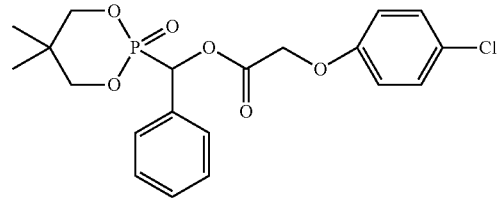 [SMILES: CC1(C)COP(=O)(C(OC(=O)COc2ccc(Cl)cc2)c2ccccc2)OC1]

The resulting pure product was white solid, with a yield of 78% and the m.p. was 58.9 to 60.2° C.
Element Analysis (%) (C₂₂H₂₂ClO₆P):
Calculated value: C, 56.55; H, 5.46.
Measured value: C, 56.93; H, 5.71.
¹H NMR (400 MHz, CDCl₃): δ 7.44-6.80 (m, 9H), 6.37-6.34 (d, 1H, J=12.0 Hz, PCHO), 4.80-4.69 (m, 2H, OCH₂CO), 4.11-3.92 (m, 4H, 2×(OCH₂)), 1.16 (s, 3H), 0.91 (s, 3H).
EI-MS m/z (%): 424 (M⁺, 1), 240 (43), 172 (4), 141 (30), 133 (85), 105 (39), 91 (7), 77 (50), 69 (100).
IR (KBr): ν 3064, 2967, 1755, 1594, 1492, 1291, 1190, 1057, 1008, 835 cm⁻¹.

Compound 29: 2-(3-methyl-4-chlorophenoxyethylacyloxy)(phenyl)methyl-5,5-dimethyl-1,3,2-dioxaphosphorinan-2-one phosphonate

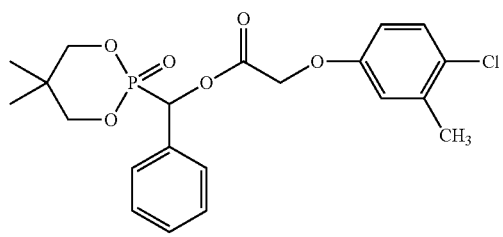 [SMILES: Cc1cc(OCC(=O)OC(c2ccccc2)P2(=O)OCC(C)(C)CO2)ccc1Cl]

The resulting pure product was faint yellow solid, with a yield of 80%, and the m.p. was 70.2 to 71.4° C.
Element Analysis (%) ($C_{21}H_{24}ClO_6P$):
Calculated value: C, 57.48; H, 5.51.
Measured value: C, 57.39; H, 5.73.
$^1$H NMR (400 MHz, CDCl$_3$): δ 7.43-6.64 (m, 8H), 6.35 (d, 1H, J=16.0 Hz, PCHO), 4.73 (d, 2H, J=2.4 Hz, OCH$_2$CO), 4.08-3.97 (m, 4H, 2×(OCH$_2$)), 2.31 (s, 3H, PhCH$_3$), 1.16 (s, 3H), 0.91 (s, 3H).
EI-MS m/z (%): 438 (M$^+$, 3), 295 (6), 241 (2), 240 (12), 175 (39), 145 (46), 133 (91), 105 (38), 91 (13), 77 (26), 69 (100).
IR (KBr): ν 3065, 2966, 1766, 1607, 1479, 1277, 1165, 1059, 1008, 837 cm$^{-1}$.

Compound 30: 2-(2,3-dimethylphenoxyethylacyloxy)(phenyl)methyl-5,5-dimethyl-1,3,2-dioxaphosphorinan-2-one phosphonate

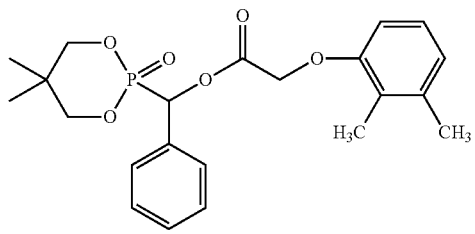

The resulting pure product was faint yellow solid, with a yield of 66%, and the m.p. was 82.2-83.5° C.
Element Analysis (%) ($C_{22}H_{27}O_6P$):
Calculated value: C, 63.15; H, 6.50.
Measured value: 62.71; H, 6.07.
$^1$H NMR (400 MHz, CDCl$_3$): δ 7.46-6.55 (m, 8H), 6.37 (d, J=12.4 Hz, 1H), 4.76 (s, 2H), 4.09-3.91 (m, 4H), 2.26 (s, 3H), 2.21 (s, 3H), 1.15 (s, 3H), 0.88 (s, 3H).
IR (KBr): ν 3068, 2969, 1776, 1586, 1497, 1273, 1184, 1058, 1010, 836 cm$^{-1}$.

Embodiment 4

Preparation of compound 31: 2-(2-fluorphenoxyethylacyloxy)(methyl)methyl-5,5-dimethyl-1,3,2-dioxaphosphorinan-2-one phosphonate

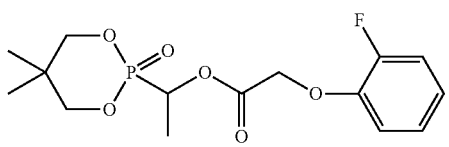 [SMILES: CC(OC(=O)COc1ccccc1F)P1(=O)OCC(C)(C)CO1]

0.003 mol of α-hydroxyalkyl phosphonate, 0.0036 mol of potassium carbonate and 10 mL of dichloroethane were cooled to below −10° C. in an ice-salt bath, and 10 mL of dichloroethane solution containing 0.0036 mol of 2,4-dichlorophenoxyacetyl chloride was added dropwise slowly. After the addition, the ice bath was removed, and the reaction solution was warmed to room temperature gradually, and refluxed at 80° C. to continue reaction. The reaction was monitored by thin layer chromatography (TLC), and was completed after about 3 hrs. After the reaction was completed, the solvent was removed directly under a reduced pressure, and the residue was washed with 20 mL of water. Then, the water phase was extracted with an appropriate amount of ethyl acetate twice, and the organic phases were combined. The mixture was dried with anhydrous sodium sulfate overnight, and after anhydrous sodium sulfate was filtered off, the solvent was removed from the filtrate to give a crude product. The crude product was recrystallized from petroleum ether and ethanol (petroleum ether:ethanol=2:3 by volume) or purified by column chromatography on silica gel (G-type) with gradient elution (eluent acetone:petroleum ether=1:8 by volume) to give a pure product.

The resulting pure product was white solid, with a yield of 87%, and the m.p. was 63 to 65° C.
Element Analysis (%) ($C_{15}H_{20}FO_6P$):
Calculated value: C, 52.03; H, 5.82.
Measured value: 52.31; H, 6.09.
$^1$H NMR (400 MHz, CDCl$_3$): δ 7.15-6.85 (m, 4H), 5.49 (m, 1H, PCHO), 4.74 (s, 2H, OCH$_2$CO), 4.15-3.99 (m, 4H, 2×(OCH$_2$)), 1.61-1.55 (q, 3H, J=7.7 Hz, PCH(CH$_3$)O), 1.17 (s, 3H), 0.99 (s, 3H).
IR (KBr): ν 3093, 2977, 1776, 1496, 1286, 1191, 1070, 1004, 952, 838, 798 cm$^{-1}$.

Compounds 32-37 were prepared by using a method similar to that of compound 31, with data of structural identification as follows:

Compound 32: 2-(3-methyl-4-chlorophenoxyethylacyloxy)(methyl)methyl-5,5-dimethyl-1,3,2-dioxaphosphorinan-2-one phosphonate

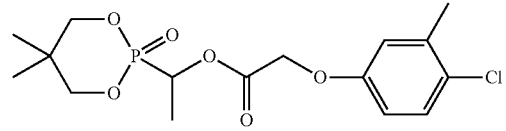 [SMILES: Cc1cc(OCC(=O)OC(C)P2(=O)OCC(C)(C)CO2)ccc1Cl]

The resulting pure product was white solid, with a yield of 88%, and the m.p. was 104 to 106° C.
Element Analysis (%) ($C_{16}H_{22}ClO_6P$):
Calculated value: C, 51.01; H, 5.89.
Measured value: C, 51.28; H, 6.03.
H NMR (600 MHz, CDCl$_3$): δ 7.25-7.23 (d, 1H, J=9.0 Hz, 5-phenyl-H), 6.78-6.64 (m, 2H, 2- and 6-phenyl-H), 5.52-5.47 (m, 1H, PCHO), 4.67 (s, 2H, OCH$_2$CO), 4.13-3.98 (m, 4H, 2×(OCH$_2$)), 2.33 (s, 3H, PhCH$_3$), 1.60-1.56 (dd, 3H, J=7.2 Hz, J=7.2 Hz, PCH(CH$_3$)O), 1.17 (s, 3H), 0.99 (s, 3H).
EI-MS m/z (%): 376 (M$^+$, 3), 178 (54), 158 (17), 155 (16), 150 (19), 133 (26), 124 (33), 111 (92), 88 (23), 69 (100).
IR (KBr): ν 3077, 2970, 1764, 1485, 1285, 1206, 1060, 1009, 953, 839, 801 cm$^{-1}$.

Compound 33: 2-(2-chlorophenoxyethylacyloxy)(methyl)methyl-5,5-dimethyl-1,3,2-dioxaphosphorinan-2-one phosphonate

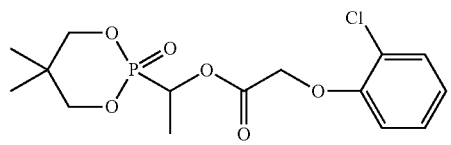

The resulting pure product was white solid, with a yield of 89%, and the m.p. was 99 to 101° C.

Element Analysis (%) ($C_{15}H_{20}ClO_6P$):
Calculated value: C, 49.67; H, 5.56.
Measured value: C, 50.03; H, 5.83.

$^1$H NMR (600 MHz, CDCl$_3$): δ 7.27-6.82 (m, 5H), 5.53-5.48 (m, 1H, PCHO), 4.70-4.68 (m, 2H, OCH$_2$CO), 4.15-3.97 (m, 4H, 2×(OCH$_2$)), 1.61-1.56 (dd, 3H, J=7.2 Hz, J=7.2 Hz, PCH(CH$_3$)O), 1.16 (s, 3H), 1.00 (s, 3H).

EI-MS m/z (%): 362 (M$^+$, 3), 178 (33), 150 (11), 141 (17), 133 (23), 111 (100), 96 (9), 75 (24), 69 (80).

IR (KBr): ν 3098, 2974, 1775, 1493, 1286, 1194, 1066, 1003, 953, 799 cm$^{-1}$.

Compound 34: 2-(2-methyl-4-chlorophenoxyethylacyloxy)(methyl)methyl-5,5-dimethyl-1,3,2-dioxaphosphorinan-2-one phosphonate

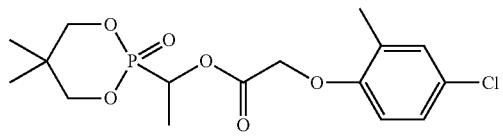 [SMILES: Cc1cc(Cl)ccc1OCC(=O)OC(C)P1(=O)OCC(C)(C)CO1]

The resulting pure product was white solid, with a yield of 86%, and the m.p. was 82.1 to 83.8° C.

Element Analysis (%) ($C_{16}H_{22}ClO_6P$):
Calculated value: C, 51.01; H, 5.89.
Measured value: C, 51.08; H, 6.23.

$^1$H NMR (600 MHz, CDCl$_3$): δ 7.14 (s, 1H, 3-phenyl-H), 7.10-7.07 (m, 1H, 5-phenyl-H), 6.61 (d, 1H, J=8.4 Hz, 6-phenyl-H), 5.50 (m, 1H, PCHO), 4.69 (d, 2H, J=4.2 Hz, OCH$_2$CO), 4.14-3.91 (m, 4H, 2×(OCH$_2$)), 2.25 (s, 3H, PhCH$_3$), 1.60-1.55 (q, 3H, J=8.4 Hz, PCH(CH$_3$)O), 1.14 (s, 3H), 1.00 (s, 3H).

EI-MS m/z (%): 376 (M$^+$, 5), 236 (4), 193 (16), 178 (38), 155 (28), 133 (49), 111 (43), 77 (37), 69 (100).

IR (KBr): ν 3079, 2972, 1768, 1491, 1231, 1184, 1056, 1010, 947, 877, 805 cm$^{-1}$.

Compound 35: 2-(4-chlorophenoxyethylacyloxy)(methyl)methyl-5,5-dimethyl-1,3,2-dioxaphosphorinan-2-one phosphonate

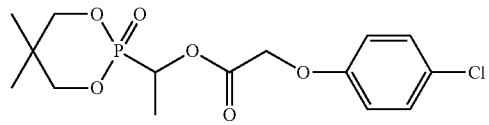 [SMILES: CC(Oc1ccc(Cl)cc1)C(=O)OC(C)P1(=O)OCC(C)(C)CO1]

The resulting pure product was white solid, with a yield of 80%, and the m.p. was 62 to 64° C.

Element Analysis (%) ($C_{15}H_{20}ClO_6P$):
Calculated value: C, 49.67; H, 5.56.
Measured value: C, 49.81; H, 5.76.

$^1$H NMR (600 MHz, CDCl$_3$): δ 7.27-7.25 (d, 2H, J=9.0 Hz, 3- and 5-phenyl-H), 6.84-6.82 (d, 2H, J=9.0 Hz, 2- and 6-phenyl-H), 5.52-5.47 (m, 1H, PCHO), 4.68 (s, 2H, OCH$_2$CO), 4.14-3.97 (m, 4H, 2×(OCH$_2$)), 1.60-1.56 (dd, 3H, J=7.2 Hz, PCH(CH$_3$)O), 1.16 (s, 3H), 1.01 (s, 3H).

$^{31}$P NMR (160 MHz, CDCl$_3$): δ 12.14.

EI-MS m/z (%): 362 (M$^+$, 5), 178 (40), 150 (11), 141 (25), 133 (33), 111 (91), 99 (6), 77 (13), 74 (18), 69 (100).

IR (KBr): ν 3093, 2976, 1776, 1495, 1286, 1191, 1070, 1004, 952, 838, 798 cm$^{-1}$.

Compound 36: 2-(2-fluor-4-chlorophenoxyethylacyloxy)(methyl)methyl-5,5-dimethyl-1,3,2-dioxaphosphorinan-2-one phosphonate

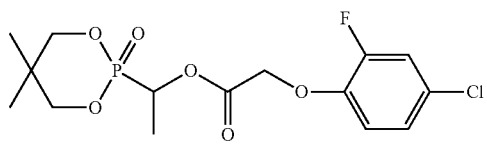 [SMILES: CC(Oc1ccc(Cl)cc1Cl)C(=O)OC(C)P1(=O)OCC(C)(C)CO1]

The resulting pure product was white solid, with a yield of 81%, and the m.p. was 107 to 109° C.

Element Analysis (%) ($C_{15}H_{19}ClFO_6P$):
Calculated value: C, 47.32; H, 5.03.
Measured value: C, 47.65; H, 5.23.

$^1$H NMR (600 MHz, CDCl$_3$): δ 7.15-6.82 (m, 3H, 3,5- and 6-phenyl-H), 5.50-5.46 (q, 1H, J=7.0 Hz, PCHO), 4.78-4.68 (dd, 2H, J=12.8 Hz, J=12.8 Hz, OCH$_2$CO), 4.14-3.99 (m, 4H, 2×(OCH$_2$)), 1.60-1.55 (dd, 3H, J=7.2 Hz, J=7.2 Hz, PCH(CH$_3$)O), 1.17 (s, 3H), 0.99 (s, 3H).

$^{31}$P NMR (160 MHz, CDCl$_3$): δ 12.36.

EI-MS m/z (%): 380 (M$^+$, 2), 235 (5), 178 (28), 159 (22), 129 (12), 111 (43), 95 (16), 83 (1), 69 (100).

IR (KBr): ν 3079, 2974, 1775, 1494, 1287, 1246, 1194, 1085, 1047, 1004, 975, 841, 798 cm$^{-1}$.

Compound 37: 2-(2-chloro-4-fluorphenoxyethylacyloxy)(methyl)methyl-5,5-dimethyl-1,3,2-dioxaphosphorinan-2-one phosphonate

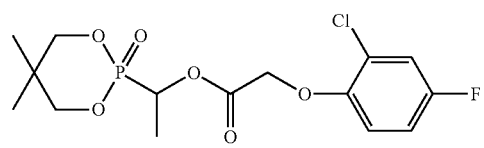

The resulting pure product was white solid, with a yield of 85%, and the m.p. was 82 to 84° C.

Element Analysis (%) ($C_{15}H_{19}ClFO_6P$):
Calculated value: C, 47.32; H, 5.03.
Measured value: C, 47.41; H, 5.30.

$^1$H NMR (600 MHz, CDCl$_3$): δ 7.17-7.15 (dd, 1H, J=2.4 Hz, J=2.4 Hz, 3-phenyl-H), 6.96-6.84 (m, 2H, 5- and 6-phenyl-H), 5.53-5.47 (m, 1H, PCHO), 4.77-4.70 (dd, 2H, J=16.8 Hz, J=16.2 Hz, OCH$_2$CO), 4.13-3.97 (m, 4H, 2×(OCH$_2$)), 1.60-1.56 (dd, 3H, J=7.2 Hz, J=6.6 Hz, PCH(CH$_3$)O), 1.16 (s, 3H), 0.99 (s, 3H).

$^{31}$P NMR (160 MHz, CDCl$_3$): δ 12.22.

EI-MS m/z (%): 380 (M$^+$, 3), 234 (5), 195 (2), 178 (31), 159 (20), 133 (23), 110 (32), 95 (14), 70 (5), 69 (100).

IR (KBr): ν 3062, 2967, 1738, 1496, 1247, 1195, 1070, 1001, 965, 829, 800 cm$^{-1}$.

Embodiment 5

Preparation of compound 38: 2-(4-chlorophenoxy-isopropylacyloxy)(methyl)methyl-5,5-dimethyl-1,3,2-dioxaphosphorinan-2-one phosphonate

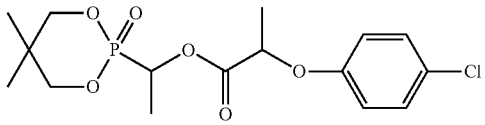

0.003 mol of α-hydroxyalkyl phosphonate, 0.0036 mol of triethyl amine and 10 mL of ethyl acetate were cooled to below −10° C. in an ice-salt bath, and 10 mL of ethyl acetate solution containing 0.0036 mol of 2,4-dichlorophenoxy-acetyl chloride was added dropwise slowly. After the addition, the ice bath was removed, and the reaction solution was warmed to room temperature gradually, and refluxed at 70° C. to continue reaction. The reaction was monitored by TLC, and was completed after about 6 hrs. After the reaction was completed, the reaction system was washed directly with 10 mL of water, the water phase was extracted with ethyl acetate twice, and the organic phases were combined. The mixture was dried with anhydrous sodium sulfate overnight, and after anhydrous sodium sulfate was filtered off, the solvent was removed from the filtrate to give a crude product. The crude product was recrystallized from petroleum ether and ethanol (petroleum ether:ethanol=2:3 by volume) or purified by column chromatography on silica gel (G-type) with gradient elution (eluent acetone:petroleum ether=1:8 by volume) to give a pure product.

The resulting pure product was white solid, with a yield of 82%, and the m.p. was 94 to 96° C.

Element Analysis (%) ($C_{16}H_{22}ClO_6P$):
Calculated value: C, 51.01; H, 5.89.
Measured value: C, 51.23; H, 6.21.
$^1$H NMR (600 MHz, CDCl$_3$): δ 7.14-6.89 (m, 4H), 5.34-5.30 (m, 1H, PCHO), 4.71-4.70 (m, 1H, OC$\underline{H}$(CH$_3$)CO), 4.10-3.88 (m, 4H, 2×(OCH$_2$)), 1.62-1.55 (dd, 3H, J=7.2 Hz, J=7.2 Hz, PCH(C$\underline{H_3}$)O), 1.54-1.47 (dd, 3H, J=7.2 Hz, J=7.2 Hz, PCH(C$\underline{H_3}$)O), 1.19 (s, 3H), 1.17 (s, 3H), 0.99 (s, 3H, major), 0.94 (s, 3H).
EI-MS m/z (%): 376 (M$^+$, 71), 267 (40), 178 (23), 169 (51), 152 (61), 128 (36), 111 (100), 95 (70), 86 (74), 69 (50).
IR (KBr): ν 3085, 2978, 1763, 1484, 1297, 1189, 1062, 1022, 953, 804 cm$^{-1}$.

Compounds 39-47 were prepared by a using a method similar to that of compound 38, with data of structural identification as follows:

Compound 39: 2-(2,4-dichlorophenoxyisopropylacyloxy)(methyl)methyl-5,5-dimethyl-1,3,2-dioxaphosphorinan-2-one phosphonate

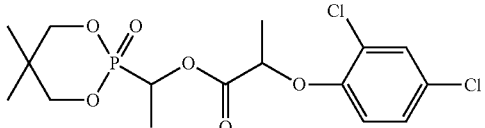

The resulting pure product was white solid, with a yield of 79%, and the m.p. was 101 to 103° C.

Element Analysis (%) ($C_{16}H_{21}Cl_2O_6P$):
Calculated value: C, 46.73; H, 5.15.
Measured value: C, 46.92; H, 5.28.
$^1$H NMR (400 MHz, CDCl$_3$): δ 7.40-7.38 (t, 1H, J=2.4 Hz, 3-phenyl-H), 7.18-7.13 (m, 1H, 5-phenyl-H), 6.83-6.75 (dd, 1H, J=8.4 Hz, J=8.8 Hz, 6-phenyl-H), 5.47-5.38 (m, 1H, PCHO), 4.82-4.74 (m, 1H, OC$\underline{H}$(CH$_3$)CO), 4.14-3.86 (m, 4H, 2×(OCH$_2$)), 1.72-1.68 (t, 3H, J=6.0 Hz, OCH(C$\underline{H_3}$)CO,), 1.61-1.54 (dd, 3H, J=7.2 Hz, J=7.2 Hz, PCH(C$\underline{H_3}$)O), 1.53-1.46 (dd, 3H, J=7.2 Hz, J=7.2 Hz, PCH(C$\underline{H_3}$)O), 1.18 (s, 3H), 1.16 (s, 3H), 0.99 (s, 3H), 0.93 (s, 3H).
$^{31}$P NMR (160 MHz, CDCl$_3$): δ 11.97;
EI-MS m/z (%): 411 (M$^+$, 2), 249 (28), 189 (13), 181 (19), 178 (15), 163 (10), 133 (43), 109 (32), 75 (6), 69 (100).
IR (KBr): ν 3075, 2973, 1760, 1480, 1290, 1190, 1052, 1011, 948, 804 cm$^{-1}$.

Compound 40: 2-(2-methyl-4-chlorophenoxyisopropylacyloxy)(methyl)methyl-5,5-dimethyl-1,3,2-dioxaphosphorinan-2-one phosphonate

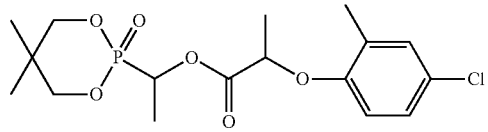 [SMILES: Cc1cc(Cl)ccc1OC(C)C(=O)OC(C)P1(=O)OCC(C)(C)CO1]

The resulting pure product was white solid, with a yield of 78%, and the m.p. was 82 to 84° C.

Element Analysis (%) ($C_{17}H_{24}ClO_6P$):
Calculated value: C, 52.25; H, 6.19.
Measured value: C, 52.45; H, 6.28.
$^1$H NMR (400 MHz, CDCl$_3$): δ 7.12-6.57 (m, 3H, 3-, 5- and 6-phenyl-H), 5.48-5.38 (m, 1H, PCHO), 4.78-4.72 (m, 1H, OC$\underline{H}$(CH$_3$)CO), 4.15-3.76 (m, 4H, 2×(OCH$_2$)), 2.24 (s, 3H, PhC$\underline{H_3}$,), 1.67-1.65 (d, 3H, J=6.8 Hz, OCH(C$\underline{H_3}$)CO), 1.60-1.54 (dd, 3H, J=7.6 Hz, J=7.2 Hz, PCH(C$\underline{H_3}$)O), 1.52-1.45 (dd, 3H, J=7.2 Hz, J=7.6 Hz, PCH(C$\underline{H_3}$)O), 1.16 (s, 3H), 1.14 (s, 3H), 0.99 (s, 3H), 0.89 (s, 3H).
$^{31}$P NMR (160 MHz, CDCl$_3$): δ 12.43.
EI-MS m/z (%): 390 (M$^+$4), 250 (19), 195(98), 178(22), 161(12), 141(20), 133(43), 111(30), 77(33), 69(91), 55 (100).
IR (KBr): ν 3096, 2973, 1760, 1491, 1246, 1186, 1052, 1010, 948, 802 cm$^{-1}$.

Compound 41: 2-(2-chloro-4-fluorphenoxyisopropylacyloxy)(methyl)methyl-5,5-dimethyl-1,3,2-dioxaphosphorinan-2-one phosphonate

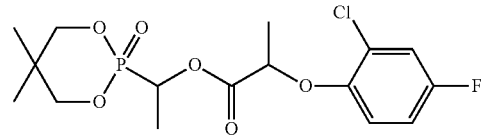 [SMILES: CC(Oc1ccc(F)cc1Cl)C(=O)OC(C)P1(=O)OCC(C)(C)CO1]

The resulting pure product was white solid, with a yield of 83%, and the m.p. was 72 to 74° C.

Element Analysis (%) ($C_{16}H_{21}ClFO_6P$):
Calculated value: C, 48.68; H, 5.36.
Measured value: C, 48.82; H, 5.58.

¹H NMR (600 MHz, CDCl₃): δ 7.16-7.14 (m, 1H, 3-phenyl-H), 6.93-6.82 (m, 2H, 5- and 6-phenyl-H), 5.47-5.40 (m, 1H, PCHO), 4.79-4.71 (m, 1H, OC$\underline{H}$(CH₃)CO), 4.14-3.88 (m, 4H, 2×(OCH₂)), 1.70-1.67 (t, 3H, J=7.8 Hz, OCH(C$\underline{H_3}$)CO), 1.59-1.55 (dd, 3H, J=7.2 Hz, J=7.2 Hz, PCH(C$\underline{H_3}$)O), 1.52-1.47 (dd, 3H, J=7.2 Hz, J=7.2 Hz, PCH(C$\underline{H_3}$)O,), 1.18 (s, 3H), 1.16 (s, 3H), 0.97 (s, 3H), 0.93 (s, 3H).

³¹P NMR (160 MHz, CDCl₃): δ 11.99.

EI-MS m/z (%): 394 (M⁺, 3), 249 (25), 195 (10), 178 (16), 173 (21), 146 (10), 133 (31), 109 (42), 91 (6), 82 (9), 69 (86), 55 (100).

IR (KBr): ν 3075, 2973, 2987, 1758, 1493, 1376, 1290, 1190, 1052, 1011, 830, 803 cm⁻¹.

Compound 42: 2-(3-methyl-4-chlorophenoxyisopropylacyloxy)(methyl)methyl-5,5-dimethyl-1,3,2-dioxaphosphorinan-2-one phosphonate

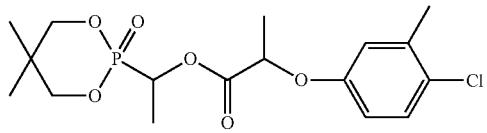 [SMILES: Cc1cc(OC(C)C(=O)OC(C)P2(=O)OCC(C)(C)CO2)ccc1Cl]

The resulting pure product was white solid, with a yield of 87%, and the m.p. was 66 to 68° C.

Element Analysis (%) (C₁₇H₂₄ClO₆P):
Calculated value: C, 52.25; H, 6.19.
Measured value: C, 52.62; H, 6.58.

¹H NMR (600 MHz, CDCl₃): δ 7.23-7.20 (dd, 1H, J=6.0 Hz, J=6.0 Hz, 5-phenyl-H), 6.76-6.61 (m, 2H, 5- and 6-phenyl-H), 5.46-5.40 (m, 1H, PCHO), 4.78-4.74 (m, 1H, OC$\underline{H}$(CH₃)CO), 4.13-3.81 (m, 4H, 2×(OCH₂)), 2.32 (s, 3H, phCH₃), 1.64-1.62 (dd, 3H, J=3.6 Hz, J=3.6 Hz, OCH(C$\underline{H_3}$)CO), 1.60-1.55 (dd, 3H, J=7.2 Hz, J=7.2 Hz, PCH(C$\underline{H_3}$)O), 1.52-1.47 (dd, 3H, J=7.2 Hz, J=7.2 Hz, PCH(C$\underline{H_3}$)O), 1.18 (s, 3H), 1.15 (s, 3H), 0.98 (s, 3H), 0.90 (s, 3H).

³¹P NMR (160 MHz, CDCl₃): δ 12.19.

EI-MS m/z (%): 390 (M⁺, 9), 249 (23), 195 (35), 169 (31), 141 (17), 133 (40), 111 (47), 89 (37), 69 (100).

IR (KBr): 3129, 2966, 1737, 1481, 1242, 1121, 1069, 995, 953, 826, 804 cm⁻¹.

Compound 43: 2-(2-chlorophenoxyisopropylacyloxy)(methyl)methyl-5,5-dimethyl-1,3,2-dioxaphosphorinan-2-one phosphonate

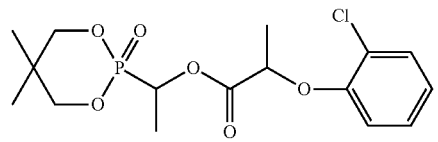 [SMILES: CC(Oc1ccccc1Cl)C(=O)OC(C)P1(=O)OCC(C)(C)CO1]

The resulting pure product was white solid, with a yield of 80%, and the m.p. was 91 to 93° C.

Element Analysis (%) (C₁₆H₂₂ClO₆P):
Calculated value: C, 51.01; H, 5.89.
Measured value: C, 51.62; H, 6.08.

¹H NMR (600 MHz, CDCl₃): δ 7.14-6.89 (m, 4H), 5.33-5.30 (m, 1H, PCHO), 4.72-4.71 (m, 1H, OC$\underline{H}$(CH₃)CO), 4.10-3.88 (m, 4H, 2×(OCH₂)), 1.62-1.55 (dd, 3H, J=7.2 Hz, J=7.2 Hz, PCH(C$\underline{H_3}$)O), 1.54-1.47 (dd, 3H, J=7.2 Hz, J=7.2 Hz, PCH(C$\underline{H_3}$)O), 1.17 (s, 3H), 1.16 (s, 3H), 0.98 (s, 3H), 0.93 (s, 3H).

³¹P NMR (160 MHz, CDCl₃): δ 12.20.

EI-MS m/z (%): 376 (M⁺, 6), 249 (21), 195 (19), 178 (40), 155 (41), 133 (31), 111 (22), 91 (33), 69 (100).

IR (KBr): ν 3127, 2977, 1740, 1491, 1247, 1121, 1067, 1007, 952, 831, 809 cm⁻¹.

Compound 44: 2-(4-fluorphenoxyisopropylacyloxy)(methyl)methyl-5,5-dimethyl-1,3,2-dioxaphosphorinan-2-one phosphonate

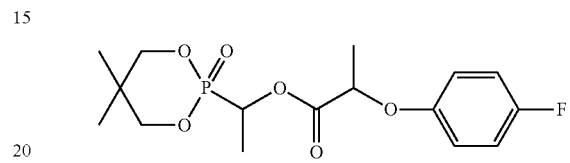

The resulting pure product was white solid, with a yield of 80%, and the m.p. was 62.1 to 63.8° C.

Element Analysis (%) (C₁₆H₂₂FO₆P):
Calculated value: C, 53.33; H, 6.15.
Measured value: C, 53.62; H, 6.58.

¹H NMR (400 MHz, CDCl₃): δ 7.00-6.94 (m, 2H, 3- and 5-phenyl-H), 6.84-6.79 (m, 2H, 2- and 6-phenyl-H), 5.45-5.40 (m, 1H, PCHO), 4.78-4.71 (m, 1H, OC$\underline{H}$(CH₃)CO), 4.11-3.82 (m, 4H, 2×(OCH₂)), 1.65-1.62 (dd, 3H, J=2.8 Hz, J=2.8 Hz, OCH(C$\underline{H_3}$)CO), 1.61-1.54 (dd, 3H, J=7.2 Hz, J=7.2 Hz, PCH(C$\underline{H_3}$)O), 1.52-1.46 (dd, 3H, J=7.2 Hz, J=6.8 Hz, PCH(C$\underline{H_3}$)O), 1.18 (s, 3H), 1.15 (s, 3H), 0.98 (s, 3H), 0.91 (s, 3H).

³¹P NMR (160 MHz, CDCl₃): δ 12.22.

EI-MS m/z (%): 360 (M⁺, 8), 249 (14), 195 (19), 178 (42), 150 (11), 139 (62), 111 (82), 95 (49), 69 (99), 55 (100).

IR (KBr): ν 3199, 3073, 2978, 1758, 1506, 1207, 1133, 1052, 1010, 950, 833, 804 cm⁻¹.

Compound 45: 2-(3-trifluormethylphenoxyethylacyloxy)(methyl)methyl-5,5-dimethyl-1,3,2-dioxaphosphorinan-2-one phosphonate

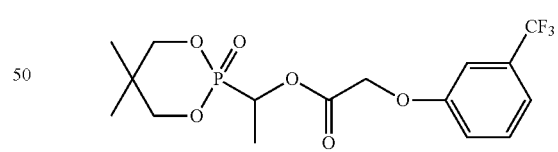

The resulting pure product was white solid, with a yield of 76%, and the m.p. was 69 to 71° C.

Element Analysis (%) (C₁₆H₂₀F₃O₆P):
Calculated value: C, 48.49; H, 5.09.
Measured value: C, 48.71; H, 5.38.

¹H NMR (400 MHz, CDCl₃): δ 7.45-7.06 (m, 4H), 5.55-5.47 (m, 1H, PCHO), 4.75 (s, 2H, OCH₂CO), 4.16-3.95 (m, 4H, 2×(OCH₂)), 1.61-1.55 (dd, 3H, J=7.2 Hz, J=7.2 Hz, PCH(C$\underline{H_3}$)O), 1.15 (s, 3H), 1.02 (s, 3H).

³¹P NMR (160 MHz, CDCl₃): δ 12.50;

EI-MS m/z (%): 396 (M⁺, 2), 201 (1), 195 (5), 178 (36), 175 (29), 150 (12), 145 (53), 133 (41), 111(39), 96 (12), 95 (7), 69 (100).

IR (KBr): ν 3094, 2974, 1767, 1594, 1494, 1331, 1171, 1065, 1012, 947, 877, 800 cm$^{-1}$.

Compound 46: 2-(4-fluorphenoxyethylacyloxy)(methyl)methyl-5,5-dimethyl-1,3,2-dioxaphosphorinan-2-one phosphonate

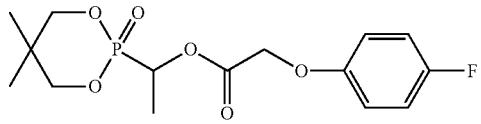 [SMILES: CC(OC(=O)COc1ccc(F)cc1)P1(=O)OCC(C)(C)CO1]

The resulting pure product was white solid, with a yield of 74%, and the m.p. was 67.5 to 69° C.

Element Analysis (%) ($C_{15}H_{20}FO_6P$):

Calculated value: C, 52.03; H, 5.82.

Measured value: C, 52.43; H, 5.95.

$^1$H NMR (600 MHz, CDCl$_3$): δ 7.01-6.83 (m, 4H), 5.53-5.49 (m, 1H, PCHO), 4.67 (s, 2H, OCH$_2$CO), 4.11-4.00 (m, 4H, 2×(OCH$_2$)), 1.60-1.56 (q, 3H, J=7.8 Hz, PCH(CH$_3$)O), 1.16 (s, 3H), 1.00 (s, 3H).

$^{31}$P NMR (160 MHz, CDCl$_3$): δ 12.42.

EI-MS m/z (%): 346 (M$^+$, 2), 195 (4), 178 (32), 150 (12), 133 (28), 125 (40), 111 (51), 95 (59), 75 (22), 69 (100).

IR (KBr): ν 3117, 2972, 1768, 1508, 1272, 1207, 1065, 1006, 952, 833, 799 cm$^{-1}$.

Compound 47: 2-(3-trifluormethylphenoxyisopropylacyloxy)(methyl)methyl-5,5-dimethyl-1,3,2-dioxaphosphorinan-2-one phosphonate

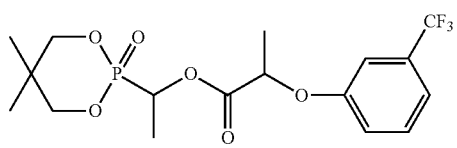 [SMILES: CC(Oc1cccc(C(F)(F)F)c1)C(=O)OC(C)P1(=O)OCC(C)(C)CO1]

The resulting pure product was white solid, with a yield of 84%, and the m.p. was 65 to 67° C.

Element Analysis (%) ($C_{17}H_{22}F_3O_6P$):

Calculated value: C, 49.76; H, 5.40.

Measured value: C, 49.92; H, 5.58.

$^1$H NMR (600 MHz, CDCl$_3$): δ 7.41-7.02 (m, 4H), 5.46-5.41 (m, 1H, PCHO), 4.87-4.83 (m, 1H, OCH(CH$_3$)CO), 4.15-3.81 (m, 4H, 2×(OCH$_2$)), 1.69-1.67 (d, 3H, J=6.6 Hz, OCH(CH$_3$)CO), 1.61-1.56 (dd, 3H, J=7.2 Hz, J=7.2 Hz, PCH(CH$_3$)O), 1.51-1.46 (dd, 3H, J=7.2 Hz, J=7.2 Hz, PCH(CH$_3$)O), 1.17 (s, 3H), 1.14 (s, 3H), 1.00 (s, 3H), 0.94 (s, 3H).

$^{31}$P NMR (160 MHz, CDCl$_3$): δ 12.22.

EI-MS m/z (%): 410 (M$^+$, 6), 249 (4), 195 (20), 189 (63), 178 (71), 150 (21), 145 (48), 141 (29), 111 (96), 96 (21), 95 (15), 69 (97), 55 (100).

IR (KBr): ν 3128, 2972, 2948, 1758, 1453, 1339, 1195, 1128, 1068, 995, 825, 796 cm$^{-1}$.

Embodiment 6

Preparation of Compound 48: 2-(phenoxyethylacyloxy)(methyl)methyl-5,5-dimethyl-1,3,2-dioxaphosphorinan-2-one phosphonate

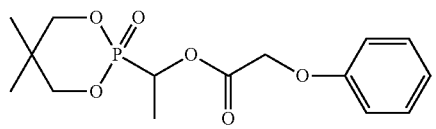 [SMILES: CC(OC(=O)COc1ccccc1)P1(=O)OCC(C)(C)CO1]

0.003 mol of α-hydroxyalkyl phosphonate, 0.0036 mol of triethyl amine and 10 mL of acetonitrile were cooled to below 10° C. in an ice-salt bath, and 10 mL of acetonitrile solution containing 0.0036 mol of 2,4-dichlorophenoxyacetyl chloride was added dropwise slowly, with a temperature constantly controlled at 5-10° C. After the addition, the ice bath was removed, and the reaction was continued after reflux at 70° C. The reaction was monitored by TLC, and was completed after about 7 hrs. After the reaction was completed, the solvent was removed directly under a reduced pressure, and the residue was washed with 20 mL of water. Then the water phase was extracted with an appropriate amount of ethyl acetate twice, and the organic phases were combined. The mixture was dried with anhydrous sodium sulfate overnight, and after anhydrous sodium sulfate was filtered off, the solvent was removed from the filtrate to give a crude product. The crude product was recrystallized from petroleum ether and ethanol (petroleum ether:ethanol=2:3 by volume) or purified by column chromatography on silica gel (G-type) with gradient elution (eluent acetone:petroleum ether=1:8 by volume) to give a pure product.

The resulting pure product was white oil, with a yield of 81%.

Element Analysis (%) ($C_{15}H_{21}O_6P$):

Calculated value: C, 54.88; H, 6.45.

Measured value: C, 55.23; H, 6.81.

$^1$H NMR (600 MHz, CDCl$_3$): δ 7.32-6.88 (m, 5H), 5.53-5.47 (m, 1H, PCHO), 4.71 (s, 2H, OCH$_2$CO), 4.12-3.98 (m, 4H, 2×(OCH$_2$)), 1.60-1.55 (dd, 3H, J=7.2 Hz, J=7.2 Hz, PCH(CH$_3$)O), 1.17 (s, 3H), 0.97 (s, 3H).

$^{31}$P NMR (160 MHz, CDCl$_3$): δ 12.26.

EI-MS m/z (%): 328 (M$^+$, 5), 195 (7), 178 (38), 150 (8), 133 (32), 111 (37), 107 (48), 96 (9), 79 (29), 77 (100), 69 (79).

IR (KBr): ν 3091, 2967, 1764, 1483, 1237, 1197, 1053, 1000, 844, 805 cm$^{-1}$.

Compounds 49-56 were prepared by using a method similar to that of compound 48, with data of structural identification as follows:

Compound 49: 2-(2-methyl-4-chlorophenoxyethylacyloxy)(2-furyl)methyl-5,5-dimethyl-1,3,2-dioxaphosphorinan-2-one phosphonate

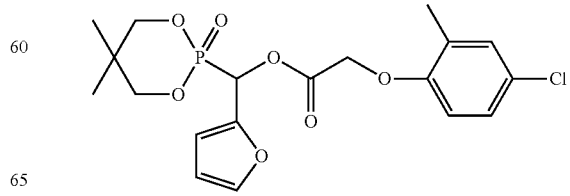

The resulting pure product was white solid, with a yield of 73%, and the m.p. was 63 to 65° C.

Element Analysis (%) ($C_{17}H_{23}Cl_2O_6P$):
Calculated value: C, 48.02; H, 5.45.
Measured value: C, 48.32; H, 5.34.

$^1$H NMR (400 MHz, CDCl$_3$): δ 7.47 (s, 1H, 5-furyl-H), 7.13-7.03 (m, 2H, 3- and 5-phenyl-H), 6.72 (s, 1H, 6-phenyl-H), 6.58-6.56 (d, 1H, J=8.4 Hz, 4-furyl-H), 6.52-6.48 (d, 1H, J=14.4 Hz, PCHO), 6.42 (s, 1H, 3-furyl-H), 4.72 (s, 1H, OCH$_2$CO), 4.11-3.98 (m, 4H, 2×(OCH$_2$)), 2.25 (s, 3H, PhCH$_3$), 1.21 (s, 3H,), 0.93 (s, 3H).

EI-MS m/z (%): 428 (M$^+$, 6), 384 (1), 278 (11), 234 (37), 230 (10), 155 (57), 125 (55), 81 (58), 69 (79).

IR (KBr): ν 3122, 2971, 1771, 1492, 1291, 1171, 1063, 1012, 947, 918, 808 cm$^{-1}$.

Compound 50: 2-(2-fluor-4-chlorophenoxyethylacyloxy)(2-furyl)methyl-5,5-dimethyl-1,3,2-dioxaphosphorinan-2-one phosphonate

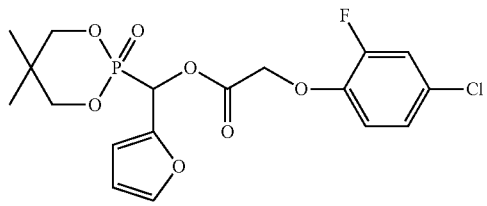 [SMILES: CC1(C)COP(=O)(C(OC(=O)COc2ccc(Cl)cc2F)c2ccco2)OC1]

The resulting pure product was white solid, with a yield of 74%, and the m.p. was 70 to 72° C.

Element Analysis (%) ($C_{18}H_{19}ClFO_7P$):
Calculated value: C, 49.96; H, 4.43.
Measured value: C, 50.05; H, 4.59.

$^1$H NMR (400 MHz, CDCl$_3$): δ 7.46 (s, 1H, 5-furyl-H), 7.17-6.80 (m, 3H, 3, 5- and 6-phenyl-H), 6.71 (s, 1H, 4-furyl-H), 6.52-6.48 (d, 1H, J=14.0 Hz, PCHO), 6.42 (s, 1H, 3-furyl-H), 4.78 (s, 1H, OCH$_2$CO), 4.18-4.03 (m, 4H, 2×(OCH$_2$)), 1.22 (s, 3H), 0.92 (s, 3H).

IR (KBr): ν 3076, 2972, 1781, 1499, 1290, 1176, 1061, 1013, 947, 859, 802 cm$^{-1}$.

Compound 51: 2-(2-chloro-4-fluorphenoxyethylacyloxy)(2-furyl)methyl-5,5-dimethyl-1,3,2-dioxaphosphorinan-2-one phosphonate

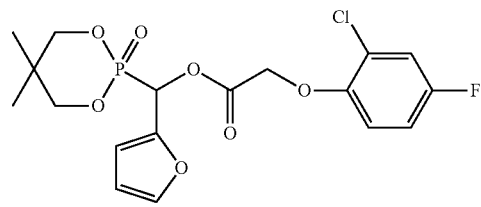 [SMILES: CC1(C)COP(=O)(C(OC(=O)COc2ccc(F)cc2Cl)c2ccco2)OC1]

The resulting pure product was white solid, with a yield of 78%, and the m.p. was 58 to 61° C.

Element Analysis (%) ($C_{18}H_{19}ClFO_7P$):
Calculated value: C, 49.96; H, 4.43.
Measured value: C, 50.15; H, 4.64.

$^1$H NMR (400 MHz, CDCl$_3$): δ 7.46 (s, 1H, 5-furyl-H), 7.16-7.13 (dd, 1H, J=3.2 Hz, J=3.2 Hz, 3-phenyl-H), 6.92-6.87 (m, 1H, 5-phenyl-H), 6.83-6.79 (dd, 1H, J=4.8 Hz, J=4.8 Hz, 6-phenyl-H), 6.71 (s, 1H, 4-furyl-H), 6.52-6.48 (d, 1H, J=14.0 Hz, PCHO), 6.42 (s, 1H, 3-furyl-H), 4.76 (s, 1H, OCH$_2$CO), 4.18-4.02 (m, 4H, 2×(OCH$_2$)), 1.22 (s, 3H), 0.93 (s, 3H).

EI-MS m/z (%): 432 (M$^+$, 21), 432 (21), 245 (60), 228 (87), 175 (9), 158 (66), 133 (100), 129 (33), 96 (21), 95 (49), 69 (76).

IR (KBr): ν 3076, 2972, 1771, 1499, 1292, 1174, 1059, 1013, 947, 861, 801 cm$^{-1}$.

Compound 52: 2-(4-fluorphenoxyethylacyloxy)(2-furyl)methyl-5,5-dimethyl-1,3,2-dioxaphosphorinan-2-one phosphonate

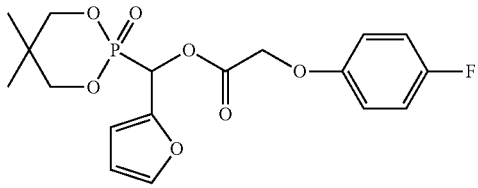 [SMILES: CC1(C)COP(=O)(C(OC(=O)COc2ccc(F)cc2)c2ccco2)OC1]

The resulting pure product was white solid, with a yield of 75%, and the m.p. was 67 to 70° C.

Element Analysis (%) ($C_{18}H_{20}FO_7P$):
Calculated value: C, 54.28; H, 5.06.
Measured value: C, 54.48; H, 5.39.

$^1$H NMR (400 MHz, CDCl$_3$): δ 7.47 (s, 1H, 5-furyl-H), 6.99-6.95 (m, 2H, 3- and 5-phenyl-H), 6.84-6.80 (m, 2H, 2- and 6-phenyl-H), 6.73-6.71 (m, 1H, 4-furyl-H), 6.53-6.49 (d, 1H, J=12.0 Hz, PCHO), 6.42-6.41 (m, 1H, 3-furyl-H), 4.69 (s, 1H, OCH$_2$CO), 4.16-4.01 (m, 4H, 2×(OCH$_2$)), 1.22 (s, 3H,), 0.94 (s, 3H).

EI-MS m/z (%): 398 (M$^+$, 5), 397 (27), 245 (37), 229 (100), 175 (14), 133 (86), 125 (82), 97 (41), 95 (96), 69 (73).

IR (KBr): ν 3077, 2972, 1770, 1506, 1290, 1173, 1061, 1012, 947, 830, 761 cm$^-$.

Compound 53: 2-(2-methyl-4-chlorophenoxyethylacyloxy)(phenyl)methyl-5,5-dimethyl-1,3,2-dioxaphosphorinan-2-one phosphonate

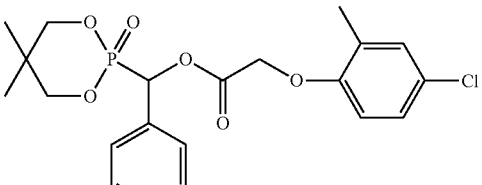

The resulting pure product was white solid, with a yield of 79%, and the m.p. was 98 to 100° C.

Element Analysis (%) ($C_{21}H_{24}ClO_6P$):
Calculated value: C, 57.48; H, 5.51.
Measured value: C, 57.59; H, 5.63.

$^1$H NMR (400 MHz, CDCl$_3$): δ 7.45-6.56 (m, 8H), 6.38-6.34 (d, 1H, J=12.0 Hz, PCHO), 4.76 (s, 2H, OCH$_2$CO), 4.11-3.86 (m, 4H, 2×(OCH$_2$)), 2.26 (s, 3H, PhCH$_3$), 1.13 (s, 3H), 0.89 (s, 3H).

EI-MS m/z (%): 438 (M$^+$, 3), 288 (12), 246 (12), 244 (41), 241 (13), 240 (84), 239 (13), 173 (24), 172 (24), 157 (18), 155

(39), 143 (15), 142 (14), 141 (29), 133 (66), 127 (20), 125 (53), 107 (17), 106 (13), 105 (41), 91 (45), 89 (28), 77 (40), 69 (100).

IR (KBr): ν 3124, 2975, 1770, 1601, 1494, 1276, 1177, 1071, 1012, 952, 837 cm$^{-1}$.

Compound 54: 2-(2-fluor-4-chlorophenoxyethylacyloxy)(phenyl)methyl-5,5-dimethyl-1,3,2-dioxaphosphorinan-2-one phosphonate

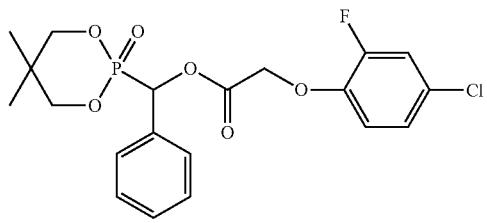 [SMILES: CC1(C)COP(=O)(C(OC(=O)COc2ccc(Cl)cc2F)c2ccccc2)OC1]

The resulting pure product was white solid, with a yield of 76%, and the m.p. 117 to 119° C.

Element Analysis (%) ($C_{20}H_{21}ClFO_6P$):

Calculated value: C, 54.25; H, 4.78.

Measured value: C, 54.55; H, 4.98.

$^1$H NMR (600 MHz, CDCl$_3$): δ 7.43-6.82 (m, 8H), 6.36-6.33 (d, 1H, J=12.0 Hz, PCHO), 4.80 (s, 2H, OCH$_2$CO), 4.10-3.96 (m, 4H, 2×(OCH$_2$)), 1.16 (s, 3H), 0.90 (s, 3H).

EI-MS m/z (%): 442 (M$^+$, 2), 279 (8), 240 (27), 161 (13), 159 (40), 146 (8), 133 (100), 131 (10), 105 (30), 77 (16), 69 (77).

IR (KBr): ν 3067, 2974, 2895, 1753, 1604, 1494, 1275, 1188, 1057, 943, 745 cm$^{-1}$.

Compound 55: 2-(2-chloro-4-fluorphenoxyethylacyloxy)(phenyl)methyl-5,5-dimethyl-1,3,2-dioxaphosphorinan-2-one phosphonate

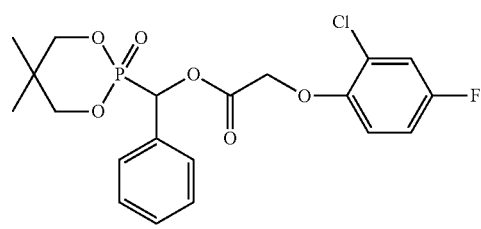 [SMILES: CC1(C)COP(=O)(C(OC(=O)COc2ccc(F)cc2Cl)c2ccccc2)OC1]

The resulting pure product was white solid, with a yield of 77%, and the m.p. was 110 to 112° C.

Element Analysis (%) ($C_{20}H_{21}ClFO_6P$):

Calculated value: C, 54.25; H, 4.78.

Measured value: C, 54.51; H, 4.93.

$^1$H NMR (400 MHz, CDCl$_3$): δ 7.45-6.81 (m, 8H), 6.38-6.34 (d, 1H, J=12.4 Hz, PCHO), 4.80 (s, 2H, OCH$_2$CO), 4.11-3.92 (m, 4H, 2×(OCH$_2$)), 1.16 (s, 3H), 0.90 (s, 3H).

EI-MS m/z (%): 442 (M$^+$, 3), 279 (9), 255 (8), 240 (78), 161 (14), 159 (45), 133 (100), 131 (10), 120 (22), 105 (31), 91 (17), 69 (85).

IR (KBr): ν 3078, 2971, 1753, 1623, 1500, 1281, 1189, 1048, 995, 839 cm$^{-1}$.

Compound 56: 2-(4-fluorphenoxyethylacyloxy)(phenyl)methyl-5,5-dimethyl-1,3,2-dioxaphosphorinan-2-one phosphonate

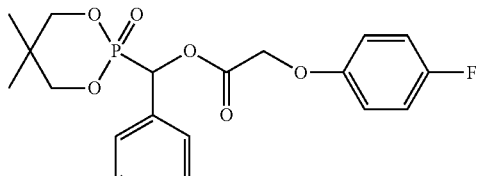

The resulting pure product was white solid, with a yield of 82%, and the m.p. was 109.8 to 113.6° C.

Element Analysis (%) ($C_{20}H_{22}FO_6P$):

Calculated value: C, 58.82; H, 5.43.

Measured value: C, 59.01; H, 5.65.

$^1$H NMR (400 MHz, CDCl$_3$): δ 7.45-6.81 (m, 9H), 6.38-6.34 (d, 1H, J=12.0 Hz, PCHO), 4.78-4.68 (dd, 2H, J=16.8 Hz, J=16.4 Hz, OCH$_2$CO), 4.11-3.93 (m, 4H, 2×(OCH$_2$)), 1.15 (s, 3H), 0.91 (s, 3H).

EI-MS m/z (%): 408 (M$^+$, 2), 240 (72), 177 (7), 133 (100), 125 (49), 95 (34), 69 (56).

IR (KBr): ν 3073, 2969, 1769, 1603, 1507, 1387, 1287, 1191, 1058, 997, 836 cm$^{-1}$.

Embodiment 7

Preparation of compound 57: 1-oxo-4-(2,4-dichlorophenoxyethylacyloxymethyl)-2,6,7-trioxa-1-phosphabicyclo[2,2,2]octane

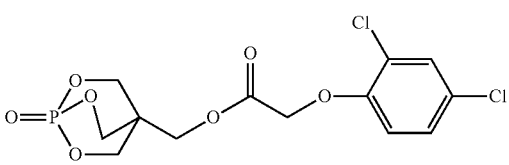

25 mL of anhydrous toluene solution dissolved with 0.005 mol of 1-oxo-4-hydroxymethyl-1-phospha-2,6,7-trioxabicyclo[2,2,2]octane and 0.006 mol of potassium carbonate were added into a 50 mL three-mouth flask, and were stirred in an ice-salt bath. 5 mL of anhydrous toluene solution dissolved with 0.005 mol of substituted phenoxyacetyl chloride was dropped in. After the dropping, the mixture was continued to be stirred for reaction for 1 h, and then heated to reflux for a complete reaction. The solvent was removed at a reduced pressure, and the resulting remaining solid was washed twice with 10 mL of water each time, to obtain a crude product, which was then recrystallized from anhydrous toluene to obtain a pure product.

The resulting pure product was white solid, with a yield of 78%, and the m.p. was 164.3 to 165.1° C.

Element Analysis (%) ($C_{13}H_{13}Cl_2O_7P$):

Calculated value: C, 40.75; H, 3.42.

Measured value: C, 40.43; H, 3.59.

$^1$H NMR (400 MHz, DMSO-d$_6$): δ 4.08 (s, 2H), 4.63 (d, J=6.4 Hz, 6H), 5.02 (s, 2H), 7.18 (d, J=8.8 Hz, 1H), 7.37 (d, J=2 Hz, 1H), 7.64 (d, J=2 Hz, 1H).
IR (KBr) ν: 1765, 1324, 1216, 1091, 1042, 963, 852, 820 cm$^{-1}$.

Compounds 58-71 were prepared by using a method similar to that of compound 57, with data of structural identification as follows:

Compound 58: 1-oxo-4-(2-chlorophenoxyethylacyloxymethyl)-2,6,7-trioxa-1-phosphabicyclo[2,2,2]octane

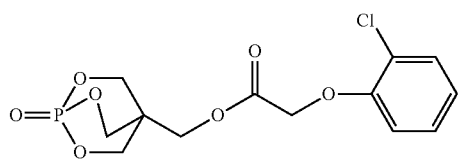

The resulting pure product was white solid, with a yield of 68%, and the m.p. was 139.8 to 142° C.
Element Analysis (%) (C$_{13}$H$_{14}$ClO$_7$P):
Calculated value: C, 44.78; H, 4.05.
Measured value: C, 44.36; H, 4.15.
$^1$H NMR (400 MHz, DMSO-d$_6$): δ 4.07 (s, 2H), 4.62 (d, J=6.4 Hz, 6H), 4.88 (s, 2H), 6.99-7.36 (m, 4H).
IR (KBr) ν: 1766, 1325, 1213, 1082, 1043, 962, 851, 827 cm$^{-1}$.

Compound 59: 1-oxo-4-(4-chlorophenoxyethylacyloxymethyl)-2,6,7-trioxa-1-phosphabicyclo[2,2,2]octane

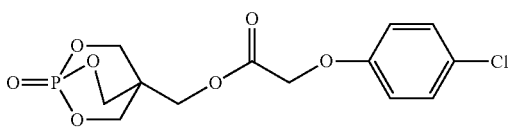

The resulting pure product was white solid, with a yield of 67%, and the m.p. was 181.6 to 182.9° C.
Element Analysis (%) (C$_{13}$H$_{14}$ClO$_7$P):
Calculated value: C, 44.78; H, 4.05.
Measured value: C, 44.60; H, 3.90.
$^1$H NMR (400 MHz, DMSO-d$_6$): δ 4.07 (s, 2H), 4.63 (d, J=6.4 Hz, 6H), 4.88 (s, 2H), 7.00 (d, J=8.4 Hz, 2H), 7.35 (d, J=8.4 Hz, 2H).
IR (KBr) ν: 1779, 1325, 1209, 1164, 1044, 965, 851, 803 cm$^{-1}$.

Compound 60: 1-oxo-4-(2-fluorphenoxyethylacyloxymethyl)-2,6,7-trioxa-1-phosphabicyclo[2,2,2]octane

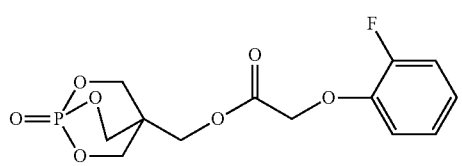 [SMILES: O=C(COc1ccccc1Cl)OCC12COP(=O)(OC1)OC2]

The resulting pure product was white solid, with a yield of 73%, and the m.p. was 147.6 to 147.9° C.
Element Analysis (%) (C$_{13}$H$_{14}$FO$_7$P):
Calculated value: C, 47.00; H, 4.25.
Measured value: C, 46.69; H, 4.41.
$^1$H NMR (400 MHz, DMSO-d$_6$): δ 4.08 (s, 2H), 4.62 (d, 6H, J=6.8 Hz), 4.96 (s, 2H), 6.99-7.28 (m, 4H).
IR (KBr) ν: 1767, 1324, 1234, 1199, 1043, 961, 850 cm$^{-1}$.

Compound 61: 1-oxo-4-(3-trifluormethylphenoxyethylacyloxymethyl)-2,6,7-trioxa-1-phosphabicyclo[2,2,2]octane

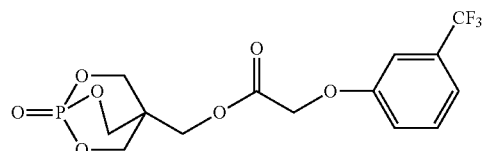

The resulting pure product was white solid, with a yield of 69%, and the m.p. 136.6-139.6° C.
Element Analysis (%) (C$_{14}$H$_{14}$F$_3$O$_7$P):
Calculated value: C, 43.99; H, 3.69.
Measured value: C, 43.28; H, 4.28.
$^1$H NMR (400 MHz, DMSO-d$_6$): δ 4.09 (s, 2H), 4.62 (d, 6H, J=6.0 Hz), 5.01 (s, 2H), 7.29-7.55 (m, 4H).
IR (KBr) ν: 1766, 1325, 1212, 1082, 1043, 962, 851, 827 cm$^{-1}$.

Compound 62: 1-oxo-4-(4-methylphenoxyethylacyloxymethyl)-2,6,7-trioxa-1-phosphabicyclo[2,2,2]octane

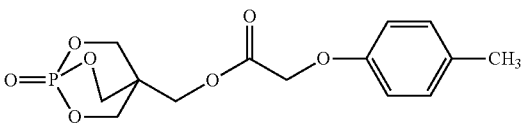 [SMILES: Cc1ccc(OCC(=O)OCC23COP(=O)(OC2)OC3)cc1]

The resulting pure product was white solid, with a yield of 71%, and the m.p. was 157.6 to 158.6° C.
Element Analysis (%) (C$_{14}$H$_{17}$O$_7$P):
Calculated value: C, 51.23; H, 5.22.
Measured value: C, 50.94; H, 51.23.
$^1$H NMR (400 MHz, DMSO-d$_6$): δ 2.23 (s, 3H), 4.06 (s, 2H), 4.60 (d, 6H, J=6.4 Hz), 4.82 (s, 2H), 6.84 (d, J=8.4 Hz, 2H), 7.10 (d, J=8.4 Hz, 2H).
IR (KBr) ν: 1766, 1326, 1214, 1087, 1043, 961, 850, 818 cm$^{-1}$.

Compound 63: 1-oxo-4-(2-methyl-4-chlorophenoxyethylacyloxymethyl)-2,6,7-trioxa-1-phosphabicyclo[2,2,2]octane

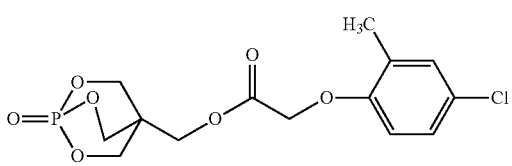

The resulting pure product was white solid, with a yield of 71%, and the m.p. was 143.3 to 144.6° C.
Element Analysis (%) ($C_{14}H_{16}ClO_7P$):
Calculated value: C, 46.36; H, 4.45.
Measured value: C, 46.37; H, 4.57.
$^1$H NMR (400 MHz, DMSO-$d_6$): δ 2.19 (s, 3H), 4.07 (s, 2H), 4.62 (d, J=6.4 Hz, 6H), 4.90 (s, 2H), 6.91-7.26 (m, 3H).
IR (KBr) ν: 1765, 1325, 1219, 1185, 1043, 962, 850, 822 cm$^{-1}$.

Compound 64: 1-oxo-4-(3-methyl-4-chlorophenoxyethylacyloxymethyl)-2,6,7-trioxa-1-phosphabicyclo[2,2,2]octane

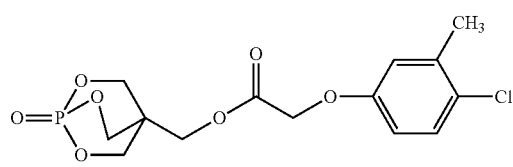 [SMILES: Cc1cc(OCC(=O)OCC23COP(=O)(OC2)OC3)ccc1Cl]

The resulting pure product was white solid, with a yield of 64.5%, and the m.p. was 122.6-123.3° C.
Element Analysis (%) ($C_{14}H_{16}ClO_7P$):
Calculated value: C, 46.36; H, 4.45.
Measured value: C, 45.99; H, 4.54.
$^1$H NMR (400 MHz, DMSO-$d_6$): δ 2.28 (s, 3H), 4.07 (s, 2H), 4.63 (d, J=6.4 Hz, 6H), 4.86 (s, 2H), 6.75-7.33 (m, 3H).
IR (KBr) ν: 1766, 1324, 1244, 1168, 1044, 962, 849, 811 cm$^{-1}$.

Compound 65: 1-oxo-4-(2-chloro-4-fluorphenoxyethylacyloxymethyl)-2,6,7-trioxa-1-phosphabicyclo[2,2,2]octane

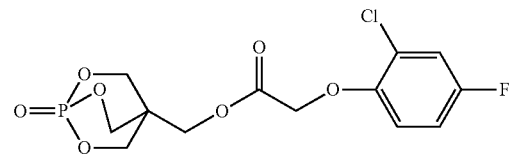 [SMILES: O=C(COc1ccc(F)cc1Cl)OCC12COP(=O)(OC1)OC2]

The resulting pure product was white solid, with a yield of 78.3%, and the m.p. was 147.5 to 151.2° C.
Element Analysis (%) ($C_{13}H_{13}FClO_7P$):
Calculated value: C, 42.58; H, 3.57.
Measured value: C, 42.51; H, 3.57.
$^1$H NMR (400 MHz, DMSO-$d_6$): δ 4.08 (s, 2H), 4.63 (d, J=6.8 Hz, 6H), 4.99 (s, 2H), 7.17-7.50 (m, 3H).
IR (KBr) ν: 1766, 1325, 1229, 1190, 1040, 963, 851 cm$^{-1}$.

Compound 66: 1-oxo-4-(2-chloro-5-methylphenoxyethylacyloxymethyl)-2,6,7-trioxa-1-phosphabicyclo[2,2,2]octane

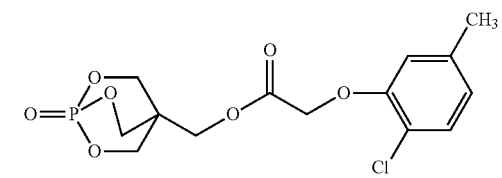 [SMILES: Cc1ccc(Cl)c(OCC(=O)OCC23COP(=O)(OC2)OC3)c1]

The resulting pure product was white solid, with a yield of 37%, and the m.p. was 170.2 to 173.4° C.
Element Analysis (%) ($C_{14}H_{16}ClO_7P$):
Calculated value: C, 46.36; H, 4.45.
Measured value: C, 46.35; H, 4.47.
$^1$H NMR (400 MHz, CDCl$_3$): δ 2.33 (s, 3H), 4.01 (s, 2H), 4.48 (d, J=6.4 Hz, 6H), 4.76 (s, 2H), 6.64-7.31 (m, 3H).
IR (KBr): 1766, 1321, 1202, 1176, 1039, 966, 852, 804 m$^{-1}$.

Compound 67: 1-oxo-4-(2,3-dimethylphenoxyethylacyloxymethyl)-2,6,7-trioxa-1-phosphabicyclo[2,2,2]octane

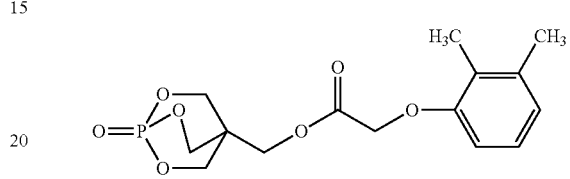

The resulting pure product was white solid, with a yield of 24%, and the m.p. was 183.3 to 184.2° C.
Element Analysis (%) ($C_{15}H_{19}O_7P$):
Calculated value: C, 52.64; H, 5.60.
Measured value: C, 52.86; H, 5.38.
$^1$H NMR (400 MHz, CDCl$_3$): δ 2.21 (s, 3H), 2.29 (s, 3H,), 3.98 (s, 2H), 4.43 (d, J=6.4 Hz 6H), 4.71 (s, 2H), 6.52-7.06 (m, 3H).
IR (KBr) ν: 1769, 1309, 1193, 1131, 1038, 970, 855 cm$^{-1}$.

Compound 68: 1-oxo-4-(4-fluorphenoxyethylacyloxymethyl)-2,6,7-trioxa-1-phosphabicyclo[2,2,2]octane

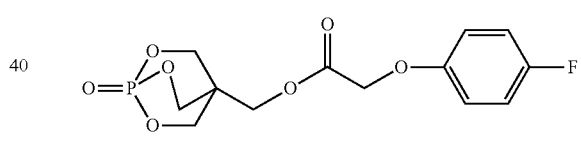

The resulting pure product was white solid, with a yield of 84%, and the m.p. was 138.6 to 140.7° C.
Element Analysis (%) ($C_{13}H_{14}FO_7P$):
Calculated value: C, 47.00; H, 4.25.
Measured value: C, 47.42; H, 4.03.
$^1$H NMR (400 MHz, CDCl$_3$): δ 4.02 (s, 2H), 4.52 (d, J=6.8 Hz, 6H), 4.66 (s, 2H), 6.85-7.02 (m, 4H).
IR (KBr) ν: 1768, 1326, 1204, 1159, 1043, 962, 850, 833 cm$^{-1}$.

Compound 69: 1-oxo-4-(3-methylphenoxyethylacyloxymethyl)-2,6,7-trioxa-1-phosphabicyclo[2,2,2]octane

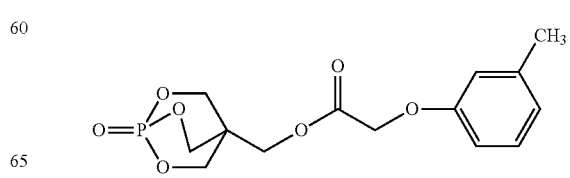

The resulting pure product was white solid, with a yield of 12%, and the m.p. was 144.6 to 144.8° C.

Element Analysis (%) ($C_{14}H_{17}O_7P$):
Calculated value: C, 51.23; H, 5.22.
Measured value: C, 51.09; H, 4.89.
$^1$H NMR (400 MHz, DMSO-$d_6$): δ 2.28 (s, 3H), 4.06 (s, 2H), 4.59 (d, J=6.4 Hz, 6H), 4.84 (s, 2H), 6.78-7.19 (m, 4H).
IR (KBr) ν: 1769, 1322, 1206, 1171, 1041, 966, 857 cm$^{-1}$.

Compound 70: 1-oxo-4-(phenoxyethylacyloxymethyl)-2,6,7-trioxa-1-phosphabicyclo[2,2,2]octane

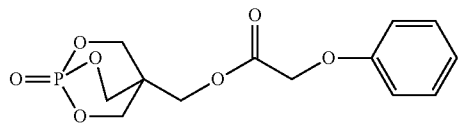

The resulting pure product was white solid, with a yield of 69%, and the m.p. was 154.6 to 155.4° C.

Element Analysis (%) ($C_{13}H_{15}O_7P$):
Calculated value: C, 49.69; H, 4.81.
Measured value: C, 49.20; H, 4.40.
$^1$H NMR (400 MHz, DMSO-$d_6$): δ 4.07 (s, 2H), 4.60 (d, J=6.4 Hz, 6H), 4.87 (s, 2H), 6.94-7.31 (m, 4H).
IR (KBr) ν: 1768, 1326, 1215, 1160, 1042, 962, 850 cm$^{-1}$.

Compound 71: 1-oxo-4-(4-tert-butylphenoxyethylacyloxymethyl)-2,6,7-trioxa-1-phosphabicyclo[2,2,2]octane

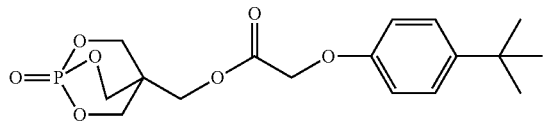 [SMILES: CC(C)(C)c1ccc(OCC(=O)OCC23COP(=O)(OC2)OC3)cc1]

The resulting pure product was white solid, with a yield of 20.7%, and the m.p. was 200.4 to 202.5° C.

Element Analysis (%) ($C_{17}H_{23}O_7P$):
Calculated value: C, 55.13; H, 6.26.
Measured value: C, 55.33; H, 5.93.
$^1$H NMR (400 MHz, DMSO-$d_6$): δ 1.25 (s, 9H), 4.05 (s, 2H), 4.55 (d, J=6.4 Hz, 6H), 4.84 (s, 2H), 6.87 (d, J=8.4 Hz, 2H), 7.31 (d, J=8 Hz, 2H).
IR (KBr) ν: 1774, 1325, 1204, 1188, 1047, 965, 852 cm$^{-1}$.

Embodiment 8

Preparation of compound 72: 1-oxo-4-(2-chloro-4-fluorphenoxyisopropylacyloxymethyl)-2,6,7-trioxa-1-phosphabicyclo[2,2,2]octane

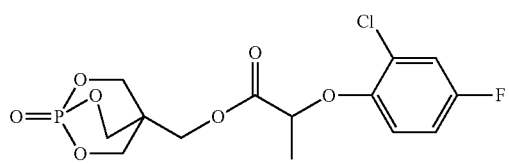 [SMILES: CC(Oc1ccc(F)cc1Cl)C(=O)OCC12COP(=O)(OC1)OC2]

25 mL of dichloromethane solution dissolved with 0.005 mol of 1-oxo-4-hydroxymethyl-1-phospha-2,6,7-trioxabicyclo[2,2,2]octane and 0.006 mol of potassium carbonate were added into a 50 mL three-mouth flask, which were stirred in an ice-salt bath. 5 mL of dichloromethane solution dissolved with 0.005 mol of substituted phenoxyacetyl chloride was dropped in. After the dropping, the mixture was continued to be stirred for reaction at room temperature for 8 hrs, until the reaction was complete. The solvent was removed at a reduced pressure, and the resulting remaining solid was washed twice with 10 mL of water each time, to obtain a crude product, which was then recrystallized from anhydrous toluene to obtain a pure product.

The resulting pure product was white solid, with a yield of 69.5%, and the m.p. was 56.4 to 58.0° C.

Element Analysis (%) ($C_{14}H_{15}ClFO_7P$):
Calculated value: C, 44.17; H, 3.97.
Measured value: C, 43.89; H, 4.17.
$^1$H NMR (600 MHz, CDCl$_3$, ppm): δ 1.66 (d, J=6.6 Hz, 3H, CH$_3$), 3.94-4.02 (q, J=12.0 Hz, 2H, —CH$_2$O—), 4.48-4.52 (m, 6H, —C(CH$_2$O)$_3$), 4.80 (q, J=7.2 Hz, 1H, —C(O)CH—), 6.853 (q, 1H, 3-phenyl-H), 6.92-6.95 (m, 1H, 5-phenyl-H), 7.19 (d, J=4.8 Hz, 1H, 6-phenyl-H).
IR (KBr) ν(cm$^{-1}$): 1751 (C=O), 1309 (P=O), 1201, 1142, 1101 (C—OC), 1042 ((P)—O—C), 967 (P—O—(C)), 852 (P(OCH$_2$)$_3$).

Compounds 73-77 were prepared by using a method similar to that of compound 72, with data of structural identification as follows:

Compound 73: 1-oxo-4-(2-fluor-4-chlorophenoxyisopropylacyloxymethyl)-2,6,7-trioxa-1-phosphabicyclo[2,2,2]octane

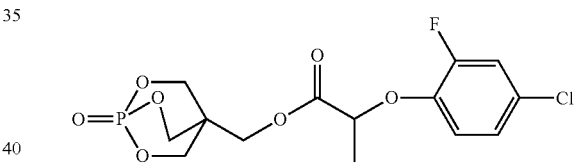

The resulting pure product was white solid, with a yield of 68.4%, and the m.p. was 107.1 to 108.0° C.

Element Analysis (%) ($C_{14}H_{15}ClFO_7P$):
Calculated value: C, 44.17; H, 3.97.
Measured value: C, 43.91; H, 4.39.
$^1$H NMR (600 MHz, CDCl$_3$, ppm): δ 1.64 (d, J=7.2 Hz, 3H, CH$_3$), 3.98 (q, J=2.4 Hz, 2H, —CH$_2$O—), 4.50-4.51 (m, 6H, —C(CH$_2$O)$_3$—), 4.81 (q, J=3.6 Hz, 1H, —C(O)CH—), 6.87-7.17 (m, 3H).
IR (KBr) ν(cm$^{-1}$): 1752 (C=O), 1320 (P=O), 1190, 1106 (C—OC), 1044 ((P)—O—C), 967 (P—O—(C)), 854 (P(OCH$_2$)$_3$).

Compound 74: 1-oxo-4-(4-fluorphenoxyisopropylacyloxymethyl)-2,6,7-trioxa-1-phosphabicyclo[2,2,2]octane

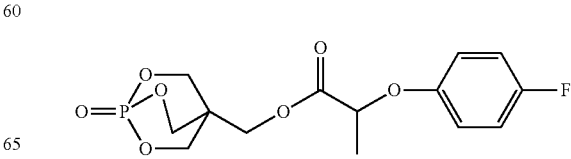

The resulting pure product was white solid, with a yield of 67.1%, and the m.p. was 106.5 to 107.5° C.

Element Analysis (%) ($C_{14}H_{16}FO_7P$):

Calculated value: C, 48.56; H, 4.66.

Measured value: C, 48.26; H, 5.16.

$^1$H NMR (600 MHz, CDCl$_3$, ppm): δ 1.62 (d, J=7.2 Hz, 3H, CH$_3$), 3.95 (q, J=25.2 Hz, 2H, —CH$_2$O—), 4.42-4.46 (m, 6H, —C(CH$_2$O)$_3$—), 4.78 (q, J=6.6 Hz, 1H, —C(O)CH—), 6.81-7.03 (m, 4H).

IR (KBr) ν(cm$^{-1}$): 1745 (C=O), 1307 (P=O), 1201, 1131, 1096 (C—OC), 1032 ((P)—O—C), 967 (P—O-(C)), 857 (P(OCH$_2$)$_3$).

Compound 75: 1-oxo-4-(2,3-dichlorophenoxyisopropylacyloxmethyl)-2,6,7-trioxa-1-phosphabicyclo[2,2,2]octane

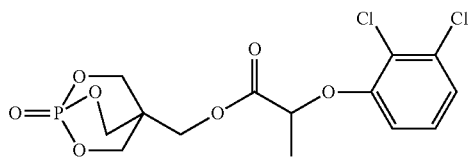

The resulting pure product was white solid, with a yield of 72.5%, and the m.p. was 185.0 to 188.5° C.

Element Analysis (%) ($C_{14}H_{15}Cl_2O_7P$):

Calculated value: C, 42.34; H, 3.81.

Measured value: C, 42.10; H, 4.29.

$^1$H NMR (600 MHz, CDCl$_3$, ppm): δ 1.70 (d, J=7.2 Hz, 3H, CH$_3$), 3.97 (q, J=22.2 Hz, 2H, —CH$_2$O—), 4.44-4.46 (m, 6H, —C(CH$_2$O)$_3$—), 4.88 (q, J=6.6 Hz, 1H, —C(O)CH—), 6.73-7.20 (m, 3H).

IR (KBr) ν(cm$^{-1}$): 1761 (C=O), 1324 (P=O), 1206, 1127, 1100 (C—O—C), 1040 ((P)—O—C), 960 (P—O—(C)), 859 (P(OCH$_2$)$_3$).

Compound 76: 1-oxo-4-(2,4-dichlorophenoxyisopropylacyloxmethyl)-2,6,7-trioxa-1-phosphabicyclo[2,2,2]octane

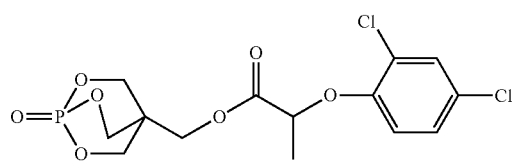 [SMILES: CC(Oc1ccc(Cl)cc1F)C(=O)OCC12COP(=O)(OC1)OC2]

The resulting pure product was white solid, with a yield of 70%, and the m.p. was 132 to 134° C.

Element Analysis (%) ($C_{14}H_{15}Cl_2O_7P$):

Calculated value: C, 42.34; H, 3.81.

Measured value: C, 42.30, H, 4.11.

$^1$H NMR (400 MHz, CDCl$_3$, ppm): δ 1.62 (d, J=6.8 Hz, 3H, CH$_3$), 3.95 (q J=14.5 Hz, 2H, —CH$_2$O—), 4.44-4.47 (m, 6H, —C(CH$_2$O)$_3$—), 4.82 (q, J=6.8 Hz, 1H, —C(O)CH—), 6.79-7.29 (m, 3H).

IR (KBr) ν(cm$^{-1}$): 1757 (C=O), 1390 (P=O), 1195, 1103 (C—O—C), 1040 ((P)—O—C), 967 (P—O—(C)), 854 (P(OCH$_2$)$_3$).

Compound 77: 1-oxo-4-(4-chlorophenoxyisopropylacyloxmethyl)-2,6,7-trioxa-1-phosphabicyclo[2,2,2]octane

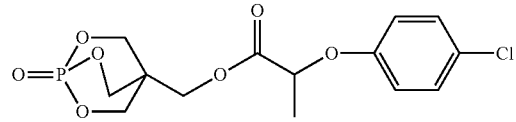 [SMILES: CC(Oc1ccc(Cl)cc1)C(=O)OCC12COP(=O)(OC1)OC2]

The resulting pure product was white solid, with a yield of 71%, and the m.p. was 148 to 150° C.

Element Analysis (%) ($C_{14}H_{16}ClO_7P$):

Calculated value: C, 46.36; H, 4.45.

Measured value: C, 46.30, H, 4.21.

$^1$H NMR (400 MHz, CDCl$_3$, ppm): δ 1.67 (d, J=6.8 Hz, 3H, CH$_3$), 3.98 (q, J=10.6 Hz, 2H, —CH$_2$O—), 4.47-4.54 (m, 6H, —C(CH$_2$O)$_3$—), 4.85 (q, J=6.6 Hz, 1H, —C(O)CH—), 6.79-7.45 (m, 4H).

IR (KBr) ν(cm$^{-1}$): 1750 (C=O), 1314 (P=O), 1244, 1210, 1132 (C—O—C), 1042 ((P)—O—C), 968 (P—O—(C)), 847 (P(OCH$_2$)$_3$).

Embodiment 9

Preparation of compound 78: 1-thio-4-(2,3-dichlorophenoxyisopropylacyloxmethyl)-2,6,7-trioxa-1-phosphabicyclo[2,2,2]octane

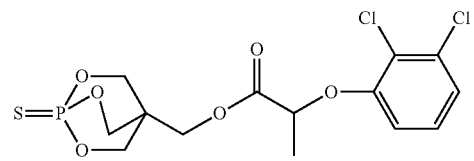 [SMILES: CC(Oc1cccc(Cl)c1Cl)C(=O)OCC12COP(=S)(OC1)OC2]

25 mL of trichloromethane toluene solution dissolved with 0.005 mol of 1-oxo-4-hydroxymethyl-1-phospha-2,6,7-trioxabicyclo[2,2,2]octane and 0.006 mol of triethyl amine were added into a 50 mL three-mouth flask, and were stirred in an ice-salt bath. 5 mL of trichloromethane solution dissolved with 0.005 mol of substituted phenoxyacetyl chloride was dropped in. After the dropping, the mixture was continued to be stirred for reaction at room temperature for 8 hrs, until the reaction was complete. The solvent was removed at a reduced pressure, and the resulting remaining solid was washed twice with 10 mL of water each time, to obtain a crude product, which was then recrystallized from anhydrous toluene to obtain a pure product.

The resulting pure product was white solid, with a yield of 69%, and the m.p. was 102 to 104° C.

Element Analysis (%) ($C_{14}H_{15}Cl_2O_6PS$):

Calculated value: C, 40.69; H, 3.66.

Measured value: C, 40.30, H, 4.01.

$^1$H NMR (400 MHz, CDCl$_3$, ppm): δ 1.63 (d, J=6.9 Hz, 3H, CH$_3$), 3.96 (q, J=18.5 Hz, 2H, —CH$_2$O—), 4.43-4.48 (m, 6H, —C(CH$_2$O)$_3$—), 4.84 (q, J=6.8 Hz, 1H, —C(O)CH—), 6.74-7.29 (m, 3H).

IR (KBr) ν(cm$^{-1}$): 1760 (C=O), 1374 (P=S), 1201, 1106 (C—O—C), 1033 ((P)—O—C), 966 (P—O—(C)), 874 (P(OCH$_2$)$_3$).

Compounds 79-83 were prepared by using a method similar to that of compound 78, with data of structural identification as follows:

Compound 79: 1-thio-4-(2,4-dichlorophenoxyisopropylacyloxmethyl)-2,6,7-trioxa-1-phosphabicyclo[2,2,2]octane

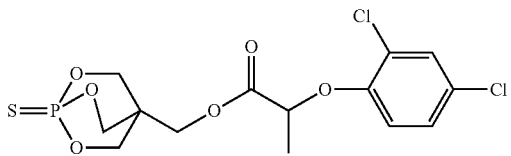 [SMILES: CC(Oc1ccc(Cl)cc1Cl)C(=O)OCC12COP(=S)(OC1)OC2]

The resulting pure product was white solid, with a yield of 65.5%, and the m.p. was 108 to 110.5° C.
Element Analysis (%) ($C_{14}H_{15}Cl_2O_6PS$):
Calculated value: C, 40.69; H, 3.66.
Measured value: C, 40.48; H, 4.03.
$^1$H NMR (600 MHz, CDCl$_3$, ppm): δ 1.67 (d, J=6.6 Hz, 3H, CH$_3$), 3.95 (q, J=12.4 Hz, 2H, —CH$_2$O—), 4.46 (t, J=6.6 Hz, 6H, —C(CH$_2$O)$_3$—), 4.84 (q, J=6.0 Hz, 1H, —C(O)CH—), 6.76-7.44 (m, 3H).
IR (KBr) ν(cm$^{-1}$): 1747 (C=O), 1266 (P=S), 1195, 1156, 1107 (C—O—C), 1034 ((P)—O—C), 971 (P—O—(C)), 869 (P(OCH$_2$)$_3$).

Compound 80: 1-thio-4-(2-fluor-4-chlorophenoxyisopropylacyloxmethyl)-2,6,7-trioxa-1-phosphabicyclo[2,2,2]octane

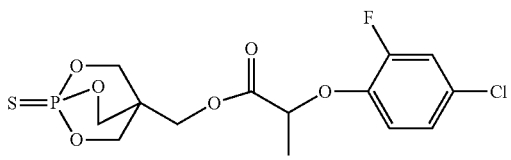 [SMILES: CC(Oc1ccc(Cl)cc1F)C(=O)OCC12COP(=S)(OC1)OC2]

The resulting pure product was white solid, with a yield of 75.8%, and the m.p. was 98.0 to 100.0° C.
Element Analysis (%) ($C_{14}H_{15}ClFO_6PS$):
Calculated value: C, 42.38; H, 3.81.
Measured value: C, 41.98; H, 4.15.
$^1$H NMR (600 MHz, CDCl$_3$, ppm): δ 1.65 (d, J=7.2 Hz, 3H, CH$_3$), 3.96 (q, J=4.8 Hz, 2H, —CH$_2$O—), 4.47 (m, 6H, —C(CH$_2$O)$_3$—), 4.841 (q, J=7.2 Hz, 1H, —C(O)CH—), 6.85-7.17 (m, 3H).
IR (KBr) ν(cm$^{-1}$): 1748 (C=O), 1269 (P=S), 1204, 1139, 1094 (C—O—C), 1024 ((P)—O—C), 970 (P—O—(C)), 867 (P(OCH$_2$)$_3$).

Compound 81: 1-thio-4-(2-chloro-4-fluorphenoxyisopropylacyloxymethyl)-2,6,7-trioxa-1-phosphabicyclo[2,2,2]octane

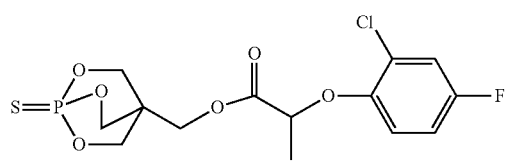 [SMILES: CC(Oc1ccc(F)cc1Cl)C(=O)OCC12COP(=S)(OC1)OC2]

The resulting pure product was white solid, with a yield of 69.7%, and the m.p. was 80.0 to 82.0° C.
Element Analysis (%) ($C_{14}H_{15}ClFO_6PS$):
Calculated value: C, 42.38; H, 3.81.
Measured value: C, 42.11; H, 3.98.
$^1$H NMR (400 MHz, CDCl$_3$, ppm): δ 1.67 (d, J=9.6 Hz, 3H, CH$_3$), 3.95 (q, J=12.8 Hz, 2H, —CH$_2$O—), 4.46 (s, 6H, —C(CH$_2$O)$_3$—), 4.80 (q, J=6.4 Hz, 1H, —C(O)CH—), 6.84-7.20 (m, 3H).
IR (KBr) ν(cm$^{-1}$): 1753 (C=O), 1260 (P=S), 1191, 1158, 1108 (C—O—C), 1033 ((P)—O—C), 973 (P—O—(C)), 868 (P(OCH$_2$)$_3$).

Compound 82: 1-thio-4-(4-fluorphenoxyisopropylacyloxymethyl)-2,6,7-trioxa-1-phosphabicyclo[2,2,2]octane

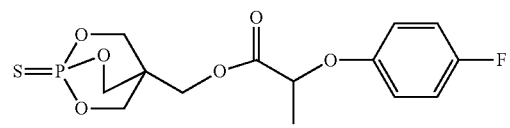 [SMILES: CC(Oc1ccc(F)cc1)C(=O)OCC12COP(=S)(OC1)OC2]

The resulting pure product was white solid, with a yield of 66.3%, and the m.p. was 119.0 to 121.0° C.
Element Analysis (%) ($C_{14}H_{16}FO_6PS$):
Calculated value: C, 46.41; H, 4.45.
Measured value: C, 46.56; H, 4.62.
$^1$H NMR (400 MHz, CDCl$_3$, ppm): δ 1.63 (d, J=2.8 Hz, 3H, CH$_3$), 3.92 (q, J=18.5 Hz, 2H, —CH$_2$O—), 4.35-4.442 (m, 6H, —C(CH$_2$O)$_3$—), 4.78 (q, J=6.8 Hz, 1H, —C(O)CH—), 6.78-7.03 (m, 4H).
IR (KBr) ν(cm$^{-1}$): 1759 (C=O), 1243 (P=S), 1145, 1102 (C—O—C), 1021 ((P)—O—C), 951 (P—O—(C)), 867 (P(OCH$_2$)$_3$).

Compound 83: 1-thio-4-(4-chlorophenoxyisopropylacyloxmethyl)-2,6,7-trioxa-1-phosphabicyclo[2,2,2]octane

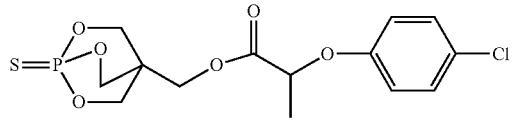 [SMILES: CC(Oc1ccc(Cl)cc1)C(=O)OCC12COP(=S)(OC1)OC2]

The resulting pure product was white solid, with a yield of 69.3%, and the m.p. was 115.0 to 117.0° C.
Element Analysis (%) ($C_{14}H_{16}ClO_6PS$):
Calculated value: C, 44.39; H, 4.26.
Measured value: C, 44.18; H, 4.48.
$^1$H NMR (400 MHz, CDCl$_3$, ppm): δ 1.63 (d, J=6.8 Hz, 3H, CH$_3$), 3.94 (q, J=13.6 Hz, 2H, —CH$_2$O—), 4.42-4.44 (m, 6H, —C(CH$_2$O)$_3$—), 4.8 (q, J=6.8 Hz, 1H, —C(O)CH—), 6.78-7.28 (m, 4H).

IR (KBr) ν(cm$^{-1}$): 1748 (C=O), 1274 (P=S), 1193, 1158, 1136 (C—O—C), 1031 ((P)—O—C), 953 (P—O—(C)), 868 (P(OCH$_2$)$_3$).

Compound 84: 2-(2,4-difluorphenoxyethylacyloxy)(phenyl)methyl-5,5-dimethyl-1,3,2-dioxaphosphorinan-2-one phosphonate

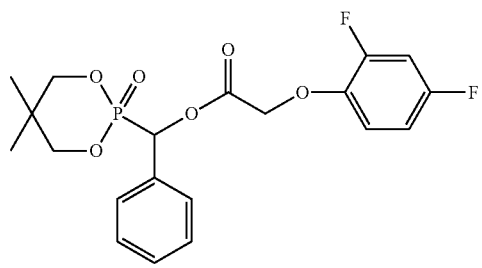 [SMILES: CC1(C)COP(=O)(C(OC(=O)COc2ccc(F)cc2F)c2ccccc2)OC1]

The resulting pure product was white solid, with a yield of 75%, and the m.p. was 79.1 to 80.8° C.
Element Analysis (%) (C$_{20}$H$_{21}$F$_2$O$_6$P):
Calculated value: C, 56.34; H, 4.96.
Measured value: C, 56.18; H, 4.83.
$^1$H NMR (600 MHz, CDCl$_3$): δ 7.45-7.37 (m, 5H, —C$_6$H$_5$), 6.90-6.71 (m, 3H, —C$_6$H$_3$), 6.35 (d, 1H, J=12.0 Hz), 4.78 (s, 2H, OCH$_2$CO), 4.08-3.87 (m, 4H, 2×(OCH$_2$)), 1.16 (s, 3H), 0.91 (s, 3H).
EI-MS m/z (%): 426 (M$^+$, 2), 263 (10), 240 (26), 195 (10), 188 (21), 150 (20), 149 (99), 143 (79), 133 (98), 69 (100), 68 (55), 67 (19).
IR (KBr): ν 3063, 2965, 2853, 1728, 1513, 1471, 1453, 1264, 1145, 1014, 965, 723 cm$^{-1}$.

Compound 85: 2-(2,4,5-trichlorophenoxyethylacyloxy)(phenyl)methyl-5,5-dimethyl-1,3,2-dioxaphosphorinan-2-one phosphonate

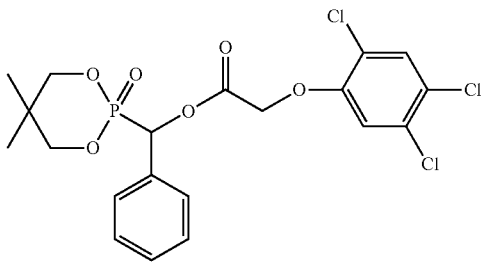 [SMILES: CC1(C)COP(=O)(C(OC(=O)COc2cc(Cl)c(Cl)cc2Cl)c2ccccc2)OC1]

The resulting pure product was faint yellow solid, with a yield of 74%, and the m.p. was 96.1 to 97.8° C.
Element Analysis (%) (C$_{20}$H$_{19}$Cl$_3$O$_6$P):
Calculated value: C, 48.66; H, 4.08.
Measured value: C, 48.51; H, 4.24.
$^1$H NMR (600 MHz, CDCl$_3$): δ 7.44-6.74 (m, 7H, —C$_6$H$_5$, —C$_6$H$_2$), 6.35 (d, J=12.0 Hz, 1H), 4.81 (s, 2H, OCH$_2$CO), 4.11-3.94 (m, 4H, 2×(OCH$_2$)), 1.14 (s, 3H), 0.93 (s, 3H).
IR (KBr): ν 3098, 2968, 2839, 1757, 1586, 1479, 1460, 1278, 1168, 1039, 945, 732 cm$^{-1}$.

Other compounds can be prepared by employing the similar methods. A part of the compounds synthetized in the present invention are listed in Table 1.

Table 1: specific structures of compounds represented by general formula I

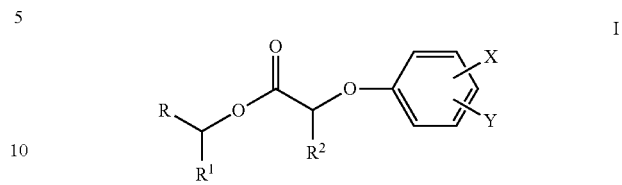

In the table: ph represents phenyl, Pyridinyl represents pyridyl, and Furyl represents furyl.

TABLE 1

Structures of compounds represented by general formula I

| No. | Q | R$^1$ | R$^2$ | X | Y |
|---|---|---|---|---|---|
| 1 | (dioxaphosphorinanone) | ph | H | 2-Cl | 4-Cl |
| 2 | (dioxaphosphorinanone) | 2-Cl—Ph | H | 2-Cl | 4-Cl |
| 3 | (dioxaphosphorinanone) | 4-Cl—Ph | H | 2-Cl | 4-Cl |
| 4 | (dioxaphosphorinanone) | 2,4-Cl$_2$Ph | H | 2-Cl | 4-Cl |
| 5 | (dioxaphosphorinanone) | 3,4-Cl$_2$Ph | H | 2-Cl | 4-Cl |
| 6 | (dioxaphosphorinanone) | 4-OCH$_3$Ph | H | 2-Cl | 4-Cl |
| 7 | (dioxaphosphorinanone) | 4-CH$_3$Ph | H | 2-Cl | 4-Cl |
| 8 | (dioxaphosphorinanone) | 4-NO$_2$Ph | H | 2-Cl | 4-Cl |
| 9 | (dioxaphosphorinanone) | 2-Pyrido | H | 2-Cl | 4-Cl |
| 10 | (dioxaphosphorinanone) | 2-Furyl | H | 2-Cl | 4-Cl |

TABLE 1-continued

Structures of compounds represented by general formula I

| No. | Q | R¹ | R² | X | Y |
|---|---|---|---|---|---|
| 11 | (cyclic phosphonate) | CH₃ | H | 2-Cl | 4-Cl |
| 12 | (cyclic phosphonate) | i-C₃H₇ | H | 2-Cl | 4-Cl |
| 13 | (cyclic phosphonate) | n-C₄H₉ | H | 2-Cl | 4-Cl |
| 14 | (cyclic phosphonate) | 2-Furyl | H | H | H |
| 15 | (cyclic phosphonate) | 2-Furyl | H | 2-Cl | H |
| 16 | (cyclic phosphonate) | 2-Furyl | H | 2-F | H |
| 17 | (cyclic phosphonate) | 2-Furyl | H | 3-CH₃ | H |
| 18 | (cyclic phosphonate) | 2-Furyl | H | 3-CF₃ | H |
| 19 | (cyclic phosphonate) | 2-Furyl | H | 4-t-Bu | H |
| 20 | (cyclic phosphonate) | 2-Furyl | H | 4-Cl | H |
| 21 | (cyclic phosphonate) | 2-Furyl | H | 4-Cl | 3-CH₃ |
| 22 | (cyclic phosphonate) | ph | H | H | H |
| 23 | (cyclic phosphonate) | ph | H | 2-Cl | H |
| 24 | (cyclic phosphonate) | ph | H | 2-F | H |
| 25 | (cyclic phosphonate) | ph | H | 3-CH₃ | H |
| 26 | (cyclic phosphonate) | ph | H | 3-CF₃ | H |
| 27 | (cyclic phosphonate) | ph | H | 4-t-Bu | H |
| 28 | (cyclic phosphonate) | ph | H | 4-Cl | H |
| 29 | (cyclic phosphonate) | ph | H | 4-Cl | 3-CH₃ |
| 30 | (cyclic phosphonate) | ph | H | 2-CH₃ | 3-CH₃ |
| 31 | (cyclic phosphonate) | CH₃ | H | 2-F | H |
| 32 | (cyclic phosphonate) | CH₃ | H | 4-Cl | 3-CH₃ |
| 33 | (cyclic phosphonate) | CH₃ | H | 2-Cl | H |
| 34 | (cyclic phosphonate) | CH₃ | H | 4-Cl | 2-CH₃ |
| 35 | (cyclic phosphonate) | CH₃ | H | 4-Cl | H |
| 36 | (cyclic phosphonate) | CH₃ | H | 2-F | 4-Cl |
| 37 | (cyclic phosphonate) | CH₃ | H | 2-Cl | 4-F |
| 38 | (cyclic phosphonate) | CH₃ | CH₃ | 4-Cl | H |

TABLE 1-continued

Structures of compounds represented by general formula I

| No. | Q | R¹ | R² | X | Y |
|---|---|---|---|---|---|
| 39 | dimethyl-dioxaphosphorinane | CH₃ | CH₃ | 2-Cl | 4-Cl |
| 40 | dimethyl-dioxaphosphorinane | CH₃ | CH₃ | 4-Cl | 2-CH₃ |
| 41 | dimethyl-dioxaphosphorinane | CH₃ | CH₃ | 2-Cl | 4-F |
| 42 | dimethyl-dioxaphosphorinane | CH₃ | CH₃ | 4-Cl | 3-CH₃ |
| 43 | dimethyl-dioxaphosphorinane | CH₃ | CH₃ | 2-Cl | H |
| 44 | dimethyl-dioxaphosphorinane | CH₃ | CH₃ | 4-F | H |
| 45 | dimethyl-dioxaphosphorinane | CH₃ | H | 3-CF₃ | H |
| 46 | dimethyl-dioxaphosphorinane | CH₃ | H | 4-F | H |
| 47 | dimethyl-dioxaphosphorinane | CH₃ | CH₃ | 3-CF₃ | H |
| 48 | dimethyl-dioxaphosphorinane | CH₃ | H | H | H |
| 49 | dimethyl-dioxaphosphorinane | 2-Furyl | H | 2-CH₃ | 4-Cl |
| 50 | dimethyl-dioxaphosphorinane | 2-Furyl | H | 2-F | 4-Cl |
| 51 | dimethyl-dioxaphosphorinane | 2-Furyl | H | 2-Cl | 4-F |
| 52 | dimethyl-dioxaphosphorinane | 2-Furyl | H | 4-F | H |
| 53 | dimethyl-dioxaphosphorinane | ph | H | 2-CH₃ | 4-Cl |
| 54 | dimethyl-dioxaphosphorinane | ph | H | 2-F | 4-Cl |
| 55 | dimethyl-dioxaphosphorinane | ph | H | 2-Cl | 4-F |
| 56 | dimethyl-dioxaphosphorinane | ph | H | 4-F | H |
| 57 | methyl-trioxaphosphabicyclooctane oxide | H | H | 2-Cl | 4-Cl |
| 58 | methyl-trioxaphosphabicyclooctane oxide | H | H | 2-Cl | H |
| 59 | methyl-trioxaphosphabicyclooctane oxide | H | H | H | 4-Cl |
| 60 | methyl-trioxaphosphabicyclooctane oxide | H | H | 2-F | H |
| 61 | methyl-trioxaphosphabicyclooctane oxide | H | H | 3-CF₃ | H |
| 62 | methyl-trioxaphosphabicyclooctane oxide | H | H | H | 4-CH₃ |
| 63 | methyl-trioxaphosphabicyclooctane oxide | H | H | 2-CH₃ | 4-Cl |
| 64 | methyl-trioxaphosphabicyclooctane oxide | H | H | 3-CH₃ | 4-Cl |
| 65 | methyl-trioxaphosphabicyclooctane oxide | H | H | 2-Cl | 4-F |
| 66 | methyl-trioxaphosphabicyclooctane oxide | H | H | 2-Cl | 5-CH₃ |

TABLE 1-continued

Structures of compounds represented by general formula I

| No. | Q | R¹ | R² | X | Y |
|---|---|---|---|---|---|
| 67 | O=P(O)(O)(O)- (CH₃) | H | H | 2-CH₃ | 3-CH₃ |
| 68 | O=P(O)(O)(O)- (CH₃) | H | H | 4-F | H |
| 69 | O=P(O)(O)(O)- (CH₃) | H | H | 3-CH₃ | H |
| 70 | O=P(O)(O)(O)- (CH₃) | H | H | H | H |
| 71 | O=P(O)(O)(O)- (CH₃) | H | H | H | 4-t-Bu |
| 72 | O=P(O)(O)(O)- (CH₃) | H | CH₃ | 2-Cl | 4-F |
| 73 | O=P(O)(O)(O)- (CH₃) | H | CH₃ | 2-F | 4-Cl |
| 74 | O=P(O)(O)(O)- (CH₃) | H | CH₃ | 4-F | H |
| 75 | O=P(O)(O)(O)- (CH₃) | H | CH₃ | 2-Cl | 3-Cl |
| 76 | O=P(O)(O)(O)- (CH₃) | H | CH₃ | 2-Cl | 4-Cl |
| 77 | O=P(O)(O)(O)- (CH₃) | H | CH₃ | H | 4-Cl |
| 78 | S=P(O)(O)(O)- (CH₃) | H | CH₃ | 2-Cl | 3-Cl |
| 79 | S=P(O)(O)(O)- (CH₃) | H | CH₃ | 2-Cl | 4-Cl |
| 80 | S=P(O)(O)(O)- (CH₃) | H | CH₃ | 2-F | 4-Cl |
| 81 | S=P(O)(O)(O)- (CH₃) | H | CH₃ | 2-Cl | 4-F |
| 82 | S=P(O)(O)(O)- (CH₃) | H | CH₃ | 4-F | H |
| 83 | S=P(O)(O)(O)- (CH₃) | H | CH₃ | 4-Cl | H |
| 84 | (dioxaphosphorinane O=P) | ph | H | 2-F | 4-F |
| 85 | (dioxaphosphorinane O=P) | ph | H | 2,4,5-Cl₃ | |

The compound of the present invention can be used as a granule, a hydrating agent, an emulsion, a flowable agent, and the like, and can also be used in mixture with or at the same time with other pesticides, fungicidals, insecticides, acaricides, plant growth regulators, fertilizers, and soil modifiers.

Embodiment 10

Weed Clearing Activity Test with Culture Dish Method

Tested agent: a sample to be tested was weighed (about 3 mg) and dissolved by adding a solvent, a drop of an emulsifier (Tween-80) was added, and diluted with distilled water to 100 µg/g and 10 µg/g.

Targets to be tested: cockspur grass and rape. Each seed was placed into a box for germination, and distilled water was added. The box was placed into a 28° C. artificial climate incubator to soak for 12 hrs. After filtering with clear water, the seed was placed into the box again for germination, and placed into a 30° C. artificial climate incubator to stimulate germination until the seed appeared white. The seed was reserved for later use.

Testing method: 9 mL of agent solutions of different concentrations were placed into 9 cm diameter culture dishes. Two sheets of filter paper that had diameters of 9 cm were added into each dish. Then 15-20 plant seeds to be tested were placed therein. After the seeds were soaked with the agent uniformly, the dishes were capped, and labeled with numbers. A blank control has equivalent amount of distilled water added instead of the agents. The culture dishes were placed into an artificial climate incubator for culturing at a temperature of 25° C. After 3 days of culturing, illumination was given for 8 hrs every day. After 5 days, root lengths and stem lengths of 10 stems of the plants that had the most flourishing growth, and overall germination situation were examined. An effect was calculated, and the drug effect was evaluated.

Effect=[(blank−treated)/blank]×100%.

Evaluation criteria: if a result is a positive value, it indicates that the agent has an inhibitory effect, and if the result is a negative value, it indicates that the agent has a promoting effect.

A test result of 1,3,2-dioxaphospha cyclic compound 1-47 of formula I, where R is structure 1, can be seen in Tables 2 and 3.

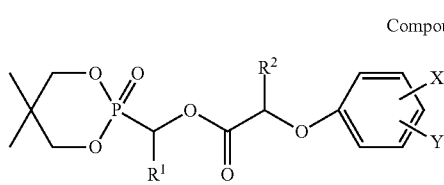

Compounds 1-30

TABLE 2

Data of weed clearing activity of compounds 1-30 of formula I (ex-vivo plate method)

| | Monocotyledonous plant cockspur grass | | | | Dicotyledonous plant rape | | | |
| | Root | | Stem | | Root | | Stem | |
| No. | 100 µg/g | 10 µg/g | 100 µg/g | 10 µg/g | 100 µg/g | 10 µg/g | 100 µg/g | 10 µg/g |
|---|---|---|---|---|---|---|---|---|
| 1 | 97 | 94 | 46 | 40 | 99 | 98 | 78 | 61 |
| 2 | 97 | 97 | 29 | 57 | 99 | 99 | 83 | 78 |
| 3 | 97 | 97 | 37 | 66 | 99 | 99 | 89 | 83 |
| 4 | 97 | 94 | 37 | 29 | 99 | 98 | 78 | 72 |
| 5 | 97 | 97 | 28 | 63 | 99 | 99 | 83 | 72 |
| 6 | 100 | 97 | 43 | 54 | 99 | 99 | 84 | 83 |
| 7 | 97 | 97 | 37 | 54 | 99 | 99 | 83 | 78 |
| 8 | 97 | 97 | 34 | 52 | 99 | 99 | 83 | 78 |
| 9 | 97 | 97 | 52 | 51 | 99 | 99 | 83 | 78 |
| 10 | 97 | 97 | 52 | 54 | 99 | 99 | 83 | 78 |
| 11 | 100 | 100 | 57 | 55 | 99 | 99 | 92 | 88 |
| 12 | 97 | 97 | 46 | 60 | 99 | 99 | 83 | 78 |
| 13 | 97 | 97 | 29 | 60 | 99 | 99 | 83 | 78 |
| 14 | 91 | 62 | 59 | 48 | 91 | 63 | 42 | 21 |
| 15 | 96 | 93 | 66 | 57 | 99 | 97 | 92 | 83 |
| 16 | 64 | 68 | 42 | 34 | 40 | 17 | 25 | 0 |
| 17 | 96 | 62 | 55 | 55 | 97 | 72 | 79 | 42 |
| 18 | 100 | 94 | 46 | 32 | 99 | 94 | 83 | 67 |
| 19 | 49 | 20 | 36 | 21 | 59 | 16 | 13 | 8 |
| 20 | 96 | 96 | 55 | 49 | 99 | 99 | 92 | 88 |
| 21 | 98 | 93 | 71 | 62 | 99 | 97 | 88 | 79 |
| 22 | 89 | 60 | 52 | 50 | 96 | 68 | 54 | 33 |
| 23 | 98 | 96 | 75 | 57 | 99 | 83 | 97 | 79 |
| 24 | 76 | 56 | 53 | 52 | 79 | 29 | 33 | 33 |
| 25 | 89 | 64 | 62 | 50 | 97 | 88 | 83 | 46 |
| 26 | 96 | 93 | 57 | 50 | 93 | 75 | 88 | 54 |
| 27 | 67 | 60 | 55 | 43 | 31 | 8 | 15 | −4 |
| 28 | 94 | 72 | 34 | 49 | 99 | 98 | 83 | 67 |
| 29 | 96 | 89 | 59 | 55 | 99 | 97 | 83 | 79 |
| 30 | 93 | 69 | 64 | 50 | 97 | 79 | 94 | 67 |

TABLE 3

Data of inhibitory activity of compounds 31-47 of formula I on plants (ex-vivo plate method, testing concentration: 100 mg/L)

| | Cockspur grass | | Sorghum | | Wheat | | Radish | | Rape | | Cucumber | |
| No. | Root | Stem | Root | Stem | Root | Stem | Root | Stem | Root | Stem | Root | Stem |
|---|---|---|---|---|---|---|---|---|---|---|---|---|
| 31 | 0 | 0 | 0 | 0 | 0 | 0 | 90 | 60 | 100 | 80 | 90 | 60 |
| 32 | 0 | 0 | 0 | 0 | 0 | 0 | 90 | 60 | 90 | 90 | 60 | 90 |
| 33 | 0 | 0 | 70 | 30 | 60 | 30 | 70 | 30 | 100 | 90 | 90 | 30 |
| 34 | 70 | 80 | 100 | 100 | 90 | 60 | 100 | 100 | 100 | 100 | 100 | 100 |
| 35 | 0 | 0 | 0 | 0 | 0 | 0 | 70 | 30 | 100 | 100 | 60 | 30 |
| 36 | 0 | 0 | 0 | 0 | 60 | 30 | 90 | 30 | 95 | 95 | 60 | 40 |
| 37 | 0 | 0 | 0 | 0 | 60 | 30 | 90 | 30 | 100 | 100 | 60 | 30 |
| 38 | 0 | 0 | 0 | 0 | 30 | 30 | 70 | 30 | 100 | 100 | 60 | 30 |
| 39 | 0 | 0 | 70 | 60 | 60 | 60 | 100 | 30 | 100 | 40 | 80 | 30 |
| 40 | 0 | 0 | 0 | 0 | 30 | 30 | 70 | 30 | 100 | 100 | 80 | 30 |
| 41 | 0 | 0 | 70 | 70 | 70 | 40 | 80 | 60 | 100 | 90 | 80 | 60 |
| 42 | 0 | 0 | 0 | 0 | 0 | 0 | 80 | 60 | 100 | 100 | 80 | 30 |
| 43 | 0 | 0 | 60 | 30 | 30 | 30 | 80 | 60 | 80 | 100 | 80 | 60 |
| 44 | 0 | 0 | 0 | 0 | 0 | 0 | 80 | 30 | 100 | 30 | 30 | 30 |
| 45 | 0 | 0 | 70 | 60 | 80 | 60 | 90 | 60 | 85 | 30 | 98 | 50 |
| 46 | 0 | 0 | 60 | 80 | 80 | 70 | 90 | 40 | 90 | 40 | 90 | 60 |
| 47 | 30 | 30 | 80 | 80 | 40 | 80 | 80 | 60 | 100 | 100 | 100 | 80 |

A test result of 1-oxo-1-phospha-2,6,7-trioxa bicyclic compound 57-77 of formula I wherein R is structure of 2 can be seen in Table 4.

Compounds 57-77

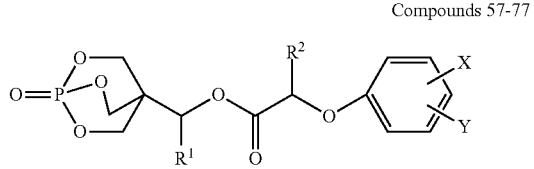

TABLE 4

Data of weed clearing activity of compounds 57-77 of formula I (ex-vivo plate method)

| | Monocotyledonous plant cockspur grass | | | | Dicotyledonous plant rape | | | |
|---|---|---|---|---|---|---|---|---|
| | Root | | Stem | | Root | | Stem | |
| No. | 100 μg/g | 10 μg/g | 100 μg/g | 10 μg/g | 100 μg/g | 10 μg/g | 100 μg/g | 10 μg/g |
| 57 | 97 | 94 | 52 | 52 | 99 | 95 | 99 | 92 |
| 58 | 97 | 91 | 55 | 48 | 99 | 95 | 97 | 90 |
| 59 | 97 | 83 | 42 | 37 | 97 | 92 | 90 | 63 |
| 60 | 80 | 69 | 55 | 31 | 92 | 53 | 49 | 24 |
| 61 | 97 | 91 | 78 | 50 | 99 | 92 | 97 | 87 |
| 62 | 94 | 51 | 22 | 4 | 97 | 79 | 88 | 34 |
| 63 | 97 | 97 | 65 | 50 | 100 | 97 | 99 | 92 |
| 64 | 97 | 91 | 63 | 55 | 100 | 97 | 97 | 90 |
| 65 | 95 | 95 | 54 | 43 | 100 | 100 | 99 | 93 |
| 66 | 93 | 54 | 37 | 3 | 99 | 93 | 88 | 75 |
| 67 | 89 | 44 | 50 | 18 | 99 | 86 | 97 | 64 |
| 68 | 94 | 89 | 78 | 18 | 99 | 86 | 97 | 64 |
| 69 | 94 | 83 | 39 | 0 | 99 | 91 | 77 | 37 |
| 70 | 94 | 89 | 82 | 0 | 99 | 82 | 83 | 23 |
| 71 | 72 | 67 | 43 | 25 | 79 | 9 | 49 | 5 |
| 72 | 97 | 94 | 59 | 28 | 99 | 98 | 94 | 90 |
| 73 | 92 | 86 | 49 | 40 | 98 | 98 | 94 | 74 |
| 74 | 96 | 88 | 50 | 25 | 99 | 96 | 93 | 79 |
| 75 | 43 | 24 | 46 | 34 | 98 | 93 | 90 | 66 |
| 76 | 91 | 85 | 43 | 30 | 97 | 94 | 93 | 71 |
| 77 | 93 | 86 | 44 | 39 | 97 | 97 | 92 | 73 |

A test result of 1-thio-1-phospha-2,6,7-trioxa bicyclic compound 78-83 of formula I, where R is structure 3, can be seen in Table 5.

Compounds 78-83

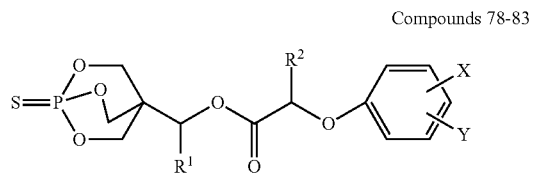

TABLE 5

Data of weed clearing activity of compounds 78-83 of formula I (ex-vivo plate method)

| | Monocotyledonous plant cockspur grass | | | | Dicotyledonous plant rape | | | |
|---|---|---|---|---|---|---|---|---|
| | Root | | Stem | | Root | | Stem | |
| No. | 100 μg/g | 10 μg/g | 100 μg/g | 10 μg/g | 100 μg/g | 10 μg/g | 100 μg/g | 10 μg/g |
| 78 | 97 | 88 | 59 | 45 | 98 | 96 | 93 | 80 |
| 79 | 97 | 91 | 54 | 37 | 99 | 97 | 93 | 89 |
| 80 | 93 | 77 | 46 | 42 | 98 | 96 | 90 | 84 |
| 81 | 97 | 79 | 47 | 40 | 98 | 96 | 93 | 62 |
| 82 | 97 | 87 | 64 | 35 | 99 | 94 | 93 | 67 |
| 83 | 97 | 93 | 43 | 36 | 99 | 97 | 96 | 91 |

Embodiment 11

Weed Clearing Activity Inhibition Experiment of Pot-Culture Method

Agent to be tested: an original agent was weighed by using an analytical balance. An emulsifier (Tween-80) and a solvent (DMF or dimethyl sulfoxide (DMSO) or water) were added and formulated into a small formulation or water aqua of 1.0-5.0% of missible oil, which was then diluted with distilled water to a concentration of 10 g/mu for later use (mu is Chinese acre).

Testing method: weed seeds to be tested were sowed into a pot that had an inner diameter of 9 cm and cultured in a greenhouse. When the dicotyledonous weed grew to a leaf period, a postemergence foliage spray was performed by using an automated sprayer. Every treatment was repeated 3 times. A blank control was set. The weed stood for 4-5 hrs after the treatment, and was transferred into the greenhouse for culturing after the agent solution on the leaf was dried. The growth situation of the plants was observed everyday, to record disease symptoms regularly, and an overall weed clearing activity was examined visually 25 days after an application of the agent.

Evaluation criteria: a visual method was used for examining the results. A degree of an effect of the agent on the growth inhibition, deformity, etiolation, decay, necrosis and the like of a plant was evaluated visually, and then the weed clearing activity was evaluated visually according to the overall disease degree by using a 0-100% grading method. Specific evaluation criteria can be seen in Table 6.

TABLE 6

Evaluation criteria for visual method of weed clearing activity

| Plant toxicity (%) | Evaluation of weed clearing activity |
|---|---|
| 0 | Being same as the control, inactive |
| 10 | Having a slight effect, very low activity |
| 20-40 | Having an effect, low activity |
| 50-70 | Significantly effecting growth, having activity |
| 80 | Severely effecting growth, leading to death in a part, having good activity |
| 90 | Severely effecting growth, leading to death in majority, a few plants remaining, having very good activity |
| 95 | Severely effecting growth, essentially leading to death in plants, few plants remaining, having very good activit |
| 100 | Leading to death of all, having very good activity |

Detailed data of in-pot postemergence weed clearing activity of a part of the compounds on the dicotyledonous plants can be seen in the following tables: compounds 1-30 in Table 7, compounds 31-47, 49-56 and 84-85 in Table 8, compounds 58-71 in Table 9, and compounds 33, 34, 37, 40, 41, and 45 in Table 10. (note: the sign/indicates that no test was carried out).

TABLE 7

Weed clearing activity of compounds 1-30 on the dicotyledonous plants (pot-culture method)

| No. | Dosage g/mu | Capsella bursa-pastoris Postemergence | Amaranthus retroflexus Postemergence | Eclipta prostrata Postemergence |
|---|---|---|---|---|
| 1 | 2.5 | 90 | 50 | 50 |
|   | 5 | 95 | 80 | 50 |
|   | 10 | 100 | 90 | 70 |
| 3 | 2.5 | 80 | 30 | 0 |
|   | 5 | 80 | 50 | 0 |
|   | 10 | 90 | 70 | 20 |
| 4 | 2.5 | 50 | 20 | 30 |
|   | 5 | 50 | 20 | 30 |
|   | 10 | 80 | 30 | 50 |
| 10 | 2.5 | 90 | 50 | 60 |
|   | 5 | 90 | 70 | 60 |
|   | 10 | 95 | 80 | 70 |
| 11 | 2.5 | 90 | 70 | 50 |
|   | 5 | 100 | 90(70) | 85(70) |
|   | 10 | 100 | 100✕ | 90✕ |
|   |   | 80 | 70 |   |
| 12 | 2.5 | 90 | 30 | 30 |
|   | 5 | 100 | 80 | 70 |
|   | 10 | 100 | 90 | 80 |
| 13 | 2.5 | 90 | 50 | 30 |
|   | 5 | 100 | 70 | 40 |
|   | 10 | 100 | 80 | 70 |
| 15 | 2.5 | 90 | 50 | 60 |
|   | 5 | 90 | 70 | 60 |
|   | 10 | 95 | 80 | 70 |
| 26 | 2.5 | 30 | 30 | 0 |
|   | 5 | 60 | 40 | 0 |
|   | 10 | 98 | 70 | 60 |

Note:
the sign ✕ in Table 7 indicates a test result of a reference expanded weed killing spectrum

TABLE 8

Postemergence weed clearing activity of compounds 31-47, 49-56 and 84-85 on the dicotyledonous plants (pot-culture method, 10 g/mu)

| No. | Capsella bursa-pastoris | Abutilon theophrasti | Amaranthus retroflexus | Eclipta prostrata |
|---|---|---|---|---|
| 31 | 75 | 70 | 70 | 70 |
| 32 | 70 | 70 | 60 | 60 |
| 33 | 100 | 70 | 90 | 75 |
| 34 | 90 | 75 | 90 | 80 |
| 35 | 75 | 70 | 70 | 60 |
| 36 | 75 | 75 | 60 | 60 |
| 37 | 95 | 90 | 90 | 85 |
| 38 | 70 | 60 | 50 | 60 |
| 39 | 80 | 70 | 70 | 60 |
| 40 | 90 | 75 | 60 | 60 |
| 41 | 90 | 70 | 60 | 60 |
| 42 | 70 | 70 | 60 | 70 |
| 43 | 70 | 70 | 60 | 60 |
| 44 | 70 | 60 | 50 | 60 |
| 45 | 85 | 75 | 50 | 50 |
| 46 | 75 | 75 | 70 | 70 |
| 47 | 75 | 75 | 60 | 50 |
| 49 | / | 100 | 100 | 70 |
| 50 | / | 70 | 70 | 70 |
| 51 | / | 100 | 100 | 90 |
| 52 | / | 85 | 30 | 40 |
| 53 | / | 100 | 100 | 75 |
| 54 | / | 75 | 80 | 75 |
| 55 | / | 100 | 100 | 70 |
| 56 | / | 40 | 70 | 70 |
| 84 | 50 | 50 | 50 | 50 |
| 85 | 60 | 50 | 50 | 50 |

TABLE 9

Postemergence weed clearing activity of compounds 58-71 on the dicotyledonous plants (pot-culture method, 10 g/mu)

| No. | Card-mine | Cassia obtusifolia | Capsella bursa-pastoris | Amaranthus retroflexus | Chenopodium serotinum | No. | Rape | Capsella bursa-pastoris | Amaranthus retroflexus | Chenopodium serotinum |
|---|---|---|---|---|---|---|---|---|---|---|
| 58 | / | / | 90 | 70 | 80 | 63 | / | 0 | 0 | 70 |
| 59 | / | / | 0 | 0 | 70 | 64 | / | 0 | 0 | 70 |
| 60 | 80 | 40 | 100 | 100 | 100 | 65 | / | 60 | 40 | 70 |
| 62 | 70 | 70 | 100 | 80 | 80 | 71 | 79 | / | 85 | / |

TABLE 10

Weed clearing activity of compounds 33, 34, 37, 40, 41 and 45 on the dicotyledonous plants (pot-culture method)

| No. | Dosage g/mu | Capsella bursa-pastoris Postemergence | Abutilon theophrasti Postemergence | Amaranthus retroflexus Postemergence | Eclipta prostrata Postemergence |
|---|---|---|---|---|---|
| 33 | 2.5 | 90 | / | 70 | 70 |
|   | 5 | 100 | 70 | 70 | 70 |
| 34 | 2.5 | / | 80 | 80 | 80 |
|   | 5 | / | 100 | 100 | 85 |

TABLE 10-continued

Weed clearing activity of compounds 33, 34, 37, 40, 41 and 45 on the dicotyledonous plants (pot-culture method)

| 37 | 2.5 | / | 70 | 60 | 60 |
|---|---|---|---|---|---|
|  | 5 | / | 100 | 100 | 85 |
| 40 | 2.5 | / | / | / | / |
|  | 5 | / | 70 | 70 | 60 |

| No. | Dosage g/mu | *Cassia obtusifolia* Postemergence | *Cardmine* Postemergence | *Capsella bursa-pastoris* Postemergence |
|---|---|---|---|---|
| 41 | 2.5 | / | / | / |
|  | 5 | / | / | / |
| 45 | 2.5 | / | / | / |
|  | 5 | / | / | / |
| 60 | 2.5 | 0 | 70 | 90 |
|  | 5 | 0 | 80 | 90 |
| 62 | 2.5 | 60 | 50 | 70 |
|  | 5 | 70 | 70 | 85 |

| No. | Dosage g/mu | *Abutilon theophrasti* Postemergence | *Amaranthus retroflexus* Postemergence | *Eclipta prostrata* Postemergence |
|---|---|---|---|---|
| 41 | 2.5 | / | / | / |
|  | 5 | 100 | 100 | 60 |
| 45 | 2.5 | / | / | / |
|  | 5 | 100 | 0 | 0 |
| 60 | 2.5 | 30 | 70 | 0 |
|  | 5 | 30 | 70 | 50 |
| 62 | 2.5 | 30 | 60 | 60 |
|  | 5 | 30 | 70 | 65 |

TABLE 11

Data of tested activity of expanded weed killing spectrum of compounds 1, 10, 11, 12, 34, 37 and 51 (pot-culture method)

Postemergence treatment

| No. | Dosage g/mu | *Vicia cracca* | Cayenne pepper | Pigweed | *Rumex acetosa* | Alligator alternanthera | *Cerastium* | Pakchoi | Tomato | Turnip | *Ipomoea purpurea* | *Ammania* | *Monochoria* | Cabbage |
|---|---|---|---|---|---|---|---|---|---|---|---|---|---|---|
| 1 | 5 | 70 | 60 | 70 | 70 | 60 | 80 | 70 | 80 | 80 | 100 | 50 | 30 | 70 |
|  | 10 | 85 | 70 | 75 | 70 | 60 | 80 | 80 | 80 | 80 | 100 | 60 | 95 | 80 |
| 10 | 5 | 70 | 60 | 70 | 75 | 60 | 70 | 70 | 80 | 80 | 100 | 100 | 100 | 80 |
|  | 10 | 80 | 70 | 80 | 80 | 70 | 75 | 80 | 80 | 85 | 100 | 100 | 100 | 85 |
| 11 | 5 | 90 | 70 | 80 | 80 | 60 | 80 | 80 | 70 | 90 | 100 | 100 | 100 | 80 |
|  | 10 | 100 | 75 | 85 | 80 | 60 | 90 | 85 | 75 | 95 | 100 | 100 | 100 | 90 |
| 12 | 5 | 70 | 75 | 75 | 70 | 60 | 70 | 70 | 80 | 80 | 100 | 80 | 70 | 70 |
|  | 10 | 90 | 75 | 75 | 80 | 60 | 80 | 90 | 85 | 98 | 100 | 90 | 80 | 70 |
| 34 | 5 | 70 | 70 | 70 | 70 | 60 | 80 | 70 | 60 | 80 | 100 | 50 | 30 | 70 |
|  | 10 | 80 | 80 | 75 | 75 | 70 | 80 | 80 | 70 | 80 | 100 | 60 | 60 | 70 |
| 37 | 5 | 70 | 60 | 80 | 70 | 60 | 80 | 80 | 100 | 80 | 100 | 60 | 50 | 70 |
|  | 10 | 80 | 75 | 80 | 75 | 60 | 80 | 80 | 100 | 80 | 100 | 90 | 90 | 80 |
| 51 | 5 | 50 | 60 | 70 | 50 | 50 | 60 | 70 | 80 | 70 | 70 | 100 | 90 | 50 |
|  | 10 | 100 | 70 | 80 | 70 | 60 | 75 | 70 | 80 | 80 | 100 | 100 | 100 | 50 |

TABLE 12

Data of tested activity of expanded weed killing spectrum of compounds 1, 10, 11, 12, 34, 37 and 51 (pot-culture method)

Postemergence treatment

| No. | Dosage g/mu | Dosage g/mu | *Abutilon theophrasti* | *Amaranthus retroflexus* | *Cucumis sativus* | *Capsella bursa-pastoris* | *Eclipta prostrata* | Rape |
|---|---|---|---|---|---|---|---|---|
| 1 | 5 | 75 | 60 | \ | 40 | \ | \ | 70 |
|  | 10 | 150 | 70 | \ | 50 | \ | \ | 80 |
| 10 | 5 | 75 | 60 | \ | 30 | \ | \ | 80 |
|  | 10 | 150 | 70 | \ | 50 | \ | \ | 95 |
| 11 | 5 | 75 | 70 | \ | 40 | \ | \ | 90 |
|  | 10 | 150 | 75 | \ | 50 | \ | \ | 100 |

TABLE 12-continued

Data of tested activity of expanded weed killing spectrum of compounds 1, 10, 11, 12, 34, 37 and 51 (pot-culture method)

| No. | Dosage g/mu | Dosage g/mu | Postemergence treatment |||||| 
|---|---|---|---|---|---|---|---|---|
| | | | *Abutilon theophrasti* | *Amaranthus retroflexus* | *Cucumis sativus* | *Capsella bursa-pastoris* | *Eclipta prostrata* | Rape |
| 12 | 5 | 75 | 60 | \ | 50 | \ | \ | 80 |
| | 10 | 150 | 70 | \ | 70 | \ | \ | 90 |
| 34 | 5 | 75 | \ | \ | 60 | 85 | \ | 80 |
| | 10 | 150 | \ | \ | 70 | \ | \ | 85 |
| 37 | 5 | 75 | \ | 90 | 60 | 80 | 60 | 70 |
| | 10 | 150 | \ | \ | 70 | \ | \ | 75 |
| 51 | 5 | 75 | 40 | 80 | 20 | 70 | 30 | 70 |
| | 10 | 150 | \ | \ | 20 | 70 | \ | 70 |

Example 12

Inhibitory Activity of a Part of Compounds I on the Crops

Test Materials:
rice, corn, cotton, soybean, rape, and wheat

A part of the compounds with higher inhibitory activity were selected to perform an evaluation on the inhibitory activity on the crop, with detailed data seen in Table 13.

TABLE 13

Data of evaluation on the inhibitory activity of the part of the compounds on the crops (10 g/mu)

| No. | $R^1$ | $R^2$ | X | Y | Rice | Corn | Cotton | Soybean | Rape | Wheat |
|---|---|---|---|---|---|---|---|---|---|---|
| 1 | Ph | H | 2-Cl | 4-Cl | 10 | 0 | 40 | 30 | 40 | 10 |
| 3 | 4-Cl-Ph | H | 2-Cl | 4-Cl | 10 | 0 | 20 | 20 | 40 | 0 |
| 4 | 2,4-diCl-Ph | H | 2-Cl | 4-Cl | 10 | 10 | 20 | 30 | 40 | 0 |
| 10 | Furyl | H | 2-Cl | 4-Cl | 40 | 0 | 30 | 30 | 40 | 10 |
| 11 | $CH_3$ | H | 2-Cl | 4-Cl | 10 | 0 | 30 | 30 | 40 | 0 |
| 12 | i-Pr | H | 2-Cl | 4-Cl | 20 | 0 | 20 | 30 | 50 | 10 |
| 13 | n-Bu | H | 2-Cl | 4-Cl | 30 | 0 | 20 | 30 | 40 | 10 |
| 26 | Ph | H | 3-$CF_3$ | H | 0 | 0 | 10 | 20 | 10 | 0 |

The test results indicate that the tested compounds have better safety in corn and wheat at a dosage of 10 g/mu.

While there has been shown several and alternate embodiments of the present invention, it is to be understood that certain changes can be made as would be known to one skilled in the art without departing from the underlying scope of the present invention as is discussed and set forth above and below including claims. Furthermore, the embodiments described above and claims set forth below are only intended to illustrate the principles of the present invention and are not intended to limit the scope of the present invention to the disclosed elements.

What is claimed is:

1. A substituted phenoxyethyl(isopropyl)acyloxyalkyl phosphonate compound comprising a phosphorusheterocyclic ring, having a structure of formula I:

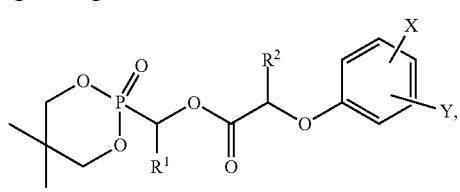

wherein in the formula I, $R^1$ represents H, $C_1$-$C_4$ alkyl, phenyl, furyl, pyridyl or phenyl substituted by substituents of methyl, methoxyl, nitro or chloro; $R^2$ represents H or methyl; X and Y represent H, halogen, $C_1$-$C_4$ alkyl, trifluoromethyl, and X and Y are different.

2. A method for preparing the substituted phenoxyethyl (isopropyl)acyloxyalkyl phosphonate compound comprising a phosphorusheterocyclic ring of formula I according to claim 1, wherein the compound of formula I is generated by reacting a compound of formula II with a compound of formula III:

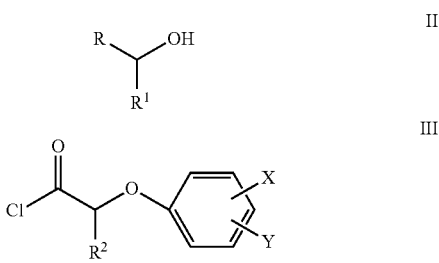

wherein in formula II,

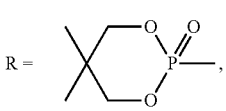

and the compound of formula I is formed as follows:

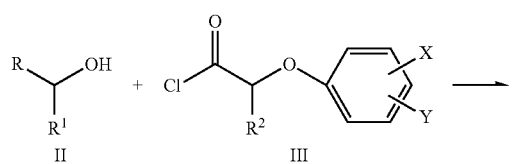

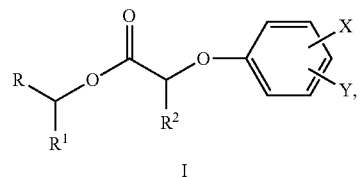

wherein in formula I, II and III, $R^1$, $R^2$, X and Y have the same definitions as the definitions of $R^1$, $R^2$, X and Y in claim 1.

3. A substituted phenoxyethyl(isopropyl)acyloxyalkyl phosphonate compound comprising a phosphorusheterocyclic ring, having a structure of formula I:

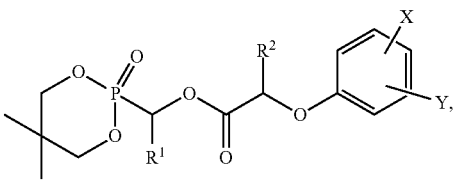

wherein in the formula I, $R^1$ represents H, $C_1$-$C_4$ alkyl, phenyl, furyl, pyridyl or phenyl substituted by substituents of methyl, methoxyl, nitro or chloro; $R^2$ represents H or methyl; X and Y represent H, halogen, $C_1$-$C_4$ alkyl, trifluoromethyl, and X and Y are the same; and wherein the structure of formula I is not

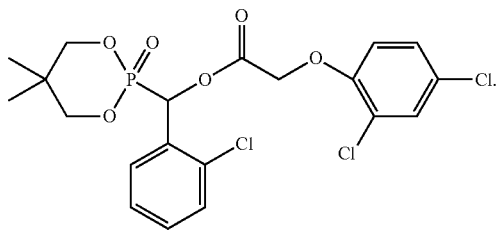 [SMILES: CC1(C)COP(=O)(C(OC(=O)COc2ccc(Cl)cc2Cl)c2ccccc2Cl)OC1]

* * * * *